United States Patent
Uber, III et al.

(10) Patent No.: US 11,648,346 B2
(45) Date of Patent: May 16, 2023

(54) MEDICAL FLUID INJECTOR

(71) Applicant: BAYER HEALTHCARE LLC, Whippany, NJ (US)

(72) Inventors: Arthur Uber, III, Pittsburgh, PA (US); Michael Yanniello, Cheswick, PA (US); Barry Tucker, Verona, PA (US); David Mishler, Slippery Rock, PA (US); Edward Rhinehart, Murrysville, PA (US); Mark Trocki, Cheswick, PA (US); Martin Uram, Pittsburgh, PA (US); John Brosovich, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 639 days.

(21) Appl. No.: 16/687,034

(22) Filed: Nov. 18, 2019

(65) Prior Publication Data
US 2020/0078518 A1 Mar. 12, 2020

Related U.S. Application Data

(60) Division of application No. 15/375,481, filed on Dec. 12, 2016, now Pat. No. 10,478,558, which is a
(Continued)

(51) Int. Cl.
*A61M 5/172* (2006.01)
*A61M 5/145* (2006.01)
*A61M 5/168* (2006.01)

(52) U.S. Cl.
CPC ........ *A61M 5/1723* (2013.01); *A61M 5/1452* (2013.01); *A61M 5/14566* (2013.01);
(Continued)

(58) Field of Classification Search
CPC ............ A61M 5/1723; A61M 5/16877; A61M 2205/18; A61M 2230/005
See application file for complete search history.

(56) References Cited

U.S. PATENT DOCUMENTS

5,383,858 A    1/1995   Reilly et al.
5,460,618 A *  10/1995  Harreld ............ A61M 25/0074
                                                 604/257
(Continued)

OTHER PUBLICATIONS

A New Technology Breakthrough PHD Ultra CP Constant Pressure Syringe Pump, Mar. 2012, Harvard Apparatus.
(Continued)

*Primary Examiner* — Bradley J Osinski
(74) *Attorney, Agent, or Firm* — David Schramm; Joseph L. Kent; James R. Stevenson

(57) ABSTRACT

Systems and methods for intelligently delivering fluid to a targeted tissue are described. The systems and methods may include directing a pump to distribute fluid to a targeted tissue and receiving one or more signals from an intracorporeal sensing system, where the one or more signals correspond to one or more sensed feedback parameters at the targeted tissue. The systems and methods may also include determining whether the one or more sensed feedback parameters are within an acceptable range. If the one or more sensed feedback parameters are not within the acceptable range, the systems and methods may include determining an adjusted velocity for the plunger necessary to adjust the pressure of the fluid in the pump so that the one or more sensed feedback parameters move within the acceptable range and directing the pump to distribute the fluid at the adjusted velocity.

16 Claims, 13 Drawing Sheets

Related U.S. Application Data continuation of application No. 13/839,864, filed on Mar. 15, 2013, now Pat. No. 9,517,305.

(52) U.S. Cl.
CPC ..... *A61M 5/16877* (2013.01); *A61M 2205/18* (2013.01); *A61M 2205/3576* (2013.01); *A61M 2205/502* (2013.01); *A61M 2205/52* (2013.01); *A61M 2230/005* (2013.01)

(56) References Cited

U.S. PATENT DOCUMENTS

| | | |
|---|---|---|
| 2006/0047318 A1 | 3/2006 | Pastore et al. |
| 2008/0166292 A1 | 7/2008 | Levin et al. |
| 2009/0226867 A1 | 9/2009 | Kalafut et al. |
| 2009/0326518 A1* | 12/2009 | Rabin ............. A61B 17/0218 606/1 |
| 2010/0204684 A1 | 8/2010 | Garrison et al. |
| 2010/0222768 A1 | 9/2010 | Spohn et al. |
| 2010/0228222 A1* | 9/2010 | Williams ............. G01G 19/414 604/113 |

OTHER PUBLICATIONS

Alino et al., Pig liver gene therapy by noninvasive interventionist catheterism, Gene Therapy, Oct. 12, 2006, pp. 334-343, vol. 14, Nature Publishing Group.

Aronovich et al., The Sleeping Beauty transposon system: a non-viral vector for gene therapy, Human Molecular Genetics, Apr. 1, 2011, vol. 20, R14-R20, Review Issue 1.

Fabre et al., Hydrodynamic gene delivery to the pig liver via an isolated segment of the inferior vena cava, Gene Therapy, Nov. 15, 2007, pp. 452-462, vol. 15, Nature Publishing Group.

International Preliminary Report on Patentability and Written Opinion dated Sep. 24, 2015 from corresponding PCT Application No. PCT/US2014/028150.

"Kamimura et al., Image-guided, Lobe-specific Hydrodynamic Gene Delivery to Swine Liver, Molecular Therapy, Jan. 20, 2009, pp. 491-499, vol. 17, No. 3".

Katsimpoulas et al., Animal Models for Hydrodynamic Gene Delivery, Chemical Biology, Feb. 17, 2012, p. 235-250, InTech.

Liu et al., Hydrodynamics-based transfection in animals by systemic administration of plasmid DNA, Gene Therapy, 1999, vol. 6, pp. 1258-1266.

Podeiz-Pedersen et al., Gene Expression in Lung and Liver After Intravenous Infusion of Polyethylenimine Complexes of Sleeping Beauty Transposons, Human Gene Therapy 21:210-220, Dec. 30, 2009.

Suda et al., Computer-assisted Hydrodynamic Gene Delivery, Molecular Therapy, 2008, pp. 1098-1104, vol. 16, No. 6.

Yoshino et al., Naked plasmid DNA transfer to the porcine liver using rapid injection with large volume, Gene Therapy, Jul. 27, 2006, vol. 13, pp. 1696-1702.

\* cited by examiner

MEDICAL FLUID INJECTOR

CROSS REFERENCE TO RELATED APPLICATIONS

This application is a Divisional of U.S. application Ser. No. 15/375,481, filed Mar. 15, 2013, which is a Continuation of U.S. application Ser. No. 13/839,864, filed Mar. 15, 2013, now U.S. Pat. No. 9,517,305, issued Dec. 13, 2016, the disclosure of which is incorporated in its entirety by this reference.

BACKGROUND

Gene therapy, in general terms, includes the use of genetic material as a pharmaceutical agent that can be used to treat disease. An illustrative form of gene therapy may include using genetic material that encodes a functional, therapeutic gene to replace a mutated gene. Other forms may include directly correcting a mutation, or using genetic material that encodes a therapeutic protein drug (rather than a natural human gene) to provide treatment. In gene therapy, the genetic material that encodes a therapeutic protein may be packaged within a vector, which is used to get the genetic material inside cells within the body. Once inside, the genetic material may become expressed by the cell machinery, which may result in the production of a therapeutic protein.

Current methods of providing gene therapy may require isolating tissue within the body of a patient with an embolization balloon catheter, and flooding the tissue with a fluid at a high flow rate and a high volume to cause secretion past capillary walls and into the tissue. This method may cause the tissue to swell to a size that is larger than its normal size. The swelling of the tissue may allow for gene therapy ingredients to be successfully injected and absorbed into the tissue. However, this method does not currently use a device that is capable of successfully injecting a sufficient amount of fluid, monitoring the pressure of the tissue to detect pressure changes, and intelligently adjusting the fluid delivery based upon the pressure changes.

BRIEF SUMMARY

In various embodiments, a system for intelligently delivering fluid to a targeted tissue may include a pump configured to contain a volume of fluid at a pressure. In some embodiments, the fluid may include one or more gene therapy ingredients. The system may also include a processor, an intracorporeal sensing system in operable communication with the processor, and a non-transitory, processor-readable storage medium in communication with the processor. The non-transitory, processor-readable storage medium may contain one or more programming instructions that, when executed, cause the processor to direct the pump to distribute the fluid to the targeted tissue at an initial velocity, receive one or more signals from the intracorporeal sensing system, where the one or more signals correspond to one or more sensed feedback parameters at the targeted tissue, and determine whether the one or more sensed feedback parameters are within an acceptable range. The sensed feedback parameters may be one or more of pressure in a receiving vessel, pressure in the targeted tissue, an image property, a tissue stretch property, a tissue conductivity, a tissue ultrasound property, a flow rate in the targeted tissue, a fluid cell count, a fluid particle count, a density of a measurable tracer, and the like. If the one or more sensed feedback parameters are not within the acceptable range, the one or more programming instructions may, when executed, cause the processor to determine an adjusted velocity for the pump necessary to adjust the pressure of the fluid in the pump so that the one or more sensed feedback parameters move within the acceptable range and direct the pump to distribute the fluid at the adjusted velocity. In some embodiments, the storage medium may further include one or more programming instructions, that, when executed, direct the processor to receive one or more inputs, wherein the one or more inputs correspond to data that defines the acceptable range.

In some embodiments, the system may also include a display in operable communication with the processor. The storage medium may further include one or more programming instructions that, when executed, direct the processor to direct the display to display data corresponding to the acceptable range in a user-readable format. The storage medium may also include one or more programming instructions that, when executed, direct the processor to direct the display to display the one or more sensed feedback parameters in a user-readable format.

In some embodiments, the system may also include one or more driving devices in operable communication with the processing device and an actuation component mechanically connected to the one or more driving devices and the pump. The storage medium may include one or more programming instructions that, when executed, cause the processor to activate the one or more driving devices to cause the actuation component to direct the pump to distribute the fluid to the targeted tissue.

In some embodiments, the pump may be a syringe body, and the system may also include a pressure jacket that is configured to surround the syringe body and prevent the syringe body from expanding. In some embodiments, the system may also include an end plug connected to a distal portion of the syringe. The end plug may be formed of a solid piece of material and may have a bore therethrough for accurate distribution of the fluid. The end plug may also be configured to prevent leakage of the fluid from the syringe body. In some embodiments, the intracorporeal sensing systems may include a sensor that is disposed at or near the targeted tissue. In some embodiments, the volume of fluid may be about 10 ml to about 2000 ml prior to distribution of the fluid to the targeted tissue, and the fluid pressure may about 10 psi to about 2000 psi prior to distribution of the fluid to the targeted tissue.

In various embodiments, a method for automatically and intelligently delivering a fluid to a targeted tissue may include directing, by a processor, a pump to distribute the fluid to the targeted tissue at an initial velocity, receiving, by the processor, one or more signals from an intracorporeal sensing system, wherein the one or more signals correspond to one or more sensed feedback parameters at the targeted tissue, and determining, by the processor, whether the one or more sensed feedback parameters are within an acceptable range. If the one or more sensed feedback parameters are not within the acceptable range, the method may also include determining, by the processor, an adjusted velocity for the pump necessary to adjust the pressure of the fluid so that the one or more sensed feedback parameters move within the acceptable range and directing, by the processor, the pump to move at the adjusted velocity. In some embodiments, the method may also include receiving, by the processor, one or more inputs, where the one or more inputs correspond to data that defines the acceptable range, directing, by the processor, a display to display data corresponding to the acceptable range in a user-readable format, and directing, by the processor, the display to display the one or more sensed feedback parameters in the user-readable format.

In some embodiments, directing pump to distribute the fluid may include causing, by the processor, one or more driving devices to activate, wherein activation of the one or more driving devices causes an actuation component to direct the pump to distribute the fluid. In some embodiments, directing the pump to distribute the fluid to the targeted tissue may further include directing the pump to distribute about 10 ml to about 2000 ml of fluid to the targeted tissue at a pressure of about 10 psi to about 2000 psi.

In various embodiments, a system for intelligently delivering fluid to a targeted tissue may include a pump configured to contain a volume of fluid at a pressure therein, a processor, an intracorporeal sensing systems in operable communication with the processor, a display in operable communication with the processor, and a non-transitory, processor-readable storage medium in communication with the processor. The non-transitory, processor-readable storage medium may contain one or more programming instructions that, when executed, cause the processor to direct the pump to distribute the fluid to the targeted tissue at an initial velocity and receive one or more signals from the intracorporeal sensing systems having a sensor distributed at or near the targeted tissue, receive one or more inputs, determine whether the one or more sensed feedback parameters are within the acceptable range, direct the display to display data corresponding to the acceptable range in a user-readable format, and direct the display to display the one or more sensed feedback parameters in the user-readable format. The one or more signals may correspond to one or more sensed feedback parameters at the targeted tissue and the one or more inputs correspond to data that defines an acceptable range. If the one or more sensed feedback parameters are not within the acceptable range, the non-transitory, processor-readable storage medium may contain one or more programming instructions that, when executed, determine an adjusted velocity for the pump necessary to adjust the pressure of the fluid in the pump so that the one or more sensed feedback parameters move within the acceptable range and direct the pump to distribute the fluid at the adjusted velocity.

BRIEF DESCRIPTION OF THE DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

Figure 1:
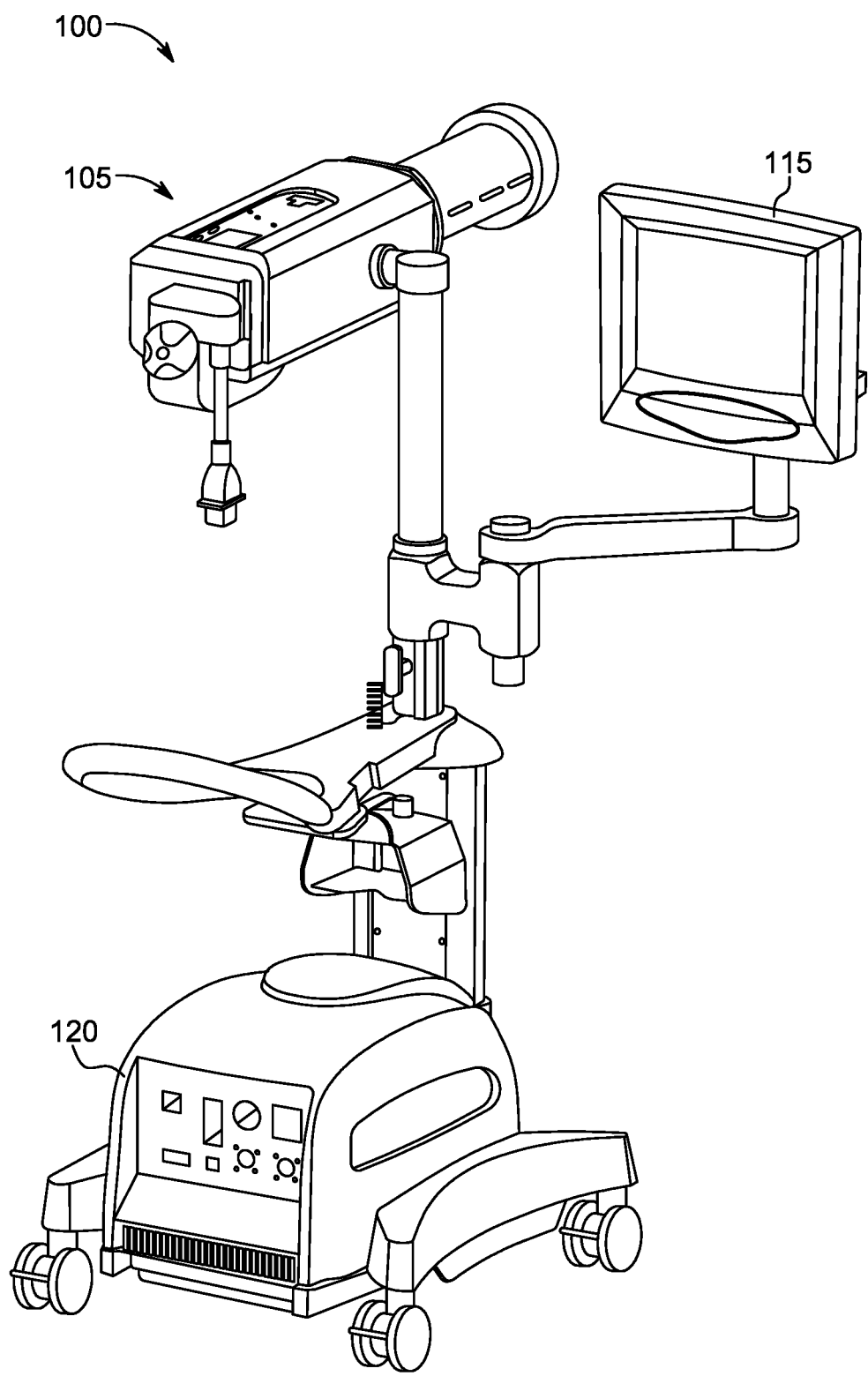
FIG. 1 depicts a perspective view of external features of a fluid delivery system according to an embodiment.

The above summary of the present disclosure is not intended to describe each illustrated embodiment or every possible implementation of the present disclosure. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

The word "proximal" refers to a direction relatively closer to a clinician or operator using the device described herein, and the word "distal" refers to a direction relatively further from the clinician or operator. For example, the end of a syringe placed nearest the body of a patient is considered a distal end of the syringe, while the end closes to the clinician is a proximal end of the syringe. The terms "axial" or "axially" refer generally to an axis around which the particular objects being referred to are preferably formed (although not necessarily symmetrically therearound). The term "radial" refers generally to a direction normal to the axis or along a radius of an object having a circular cross-section.

The word "subject" refers to one or more persons and/or animals receiving treatment from the apparatus and/or components disclosed herein according to various embodiments. The subject may be any human patient, male or female, of any age, race, height, or weight. In addition, the subject may be any species of animal, including, but not limited to, dogs, horses, cows, pigs, rats, mice, and the like.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

The systems described herein may be used for treatment of any type of tissue, particularly tissue that is amenable to gene therapy treatment. Illustrative examples of tissue that may be used may include, but are not limited to, liver tissue, muscle tissue, brain tissue, and tumor tissue. The liver is an illustrative tissue used as a pathway in gene therapy to deliver a drug as a treatment for various diseases and disorders through the introduction of an altered gene. To effectively administer the treatment, the liver vasculature is injected with a rapid delivery that permeates the capillary wall of the liver to allow penetration of the delivery drug. At some point during the drug delivery, beyond or including that necessary to achieve the desired extravasation of the delivery, the capillary and cell walls may become damaged. Although damage can be measured post-injection, damage detection cannot be determined immediately. Measurement of elevated transaminases, such as, for example, aspartate aminotransferase (AST) and alanine aminotransferase (ATL) may indicate the extent of damage, but may only be present up to 6 to 8 hours following the procedure. The elevated ATL and AST levels are indicative of enzymes that are released during repair of the damage. In order to prevent unnecessary or extended liver damage, a change in the in vivo pressure can be used as an event to determine the management of the delivery to minimize liver damage. The change that occurs is typically a drop in pressure, but a rapid increase can be used to determine an occlusion as well. As a simple control, the injection can terminate, continue forward for a timed amount, or operated in a "keep the vein open" (KVO) mode to maintain a reduced pressure until saturation is achieved. The use of statistical (i.e., historic) data along with weight, size, and other diagnostic information can be used to fine-tune the procedure.

Various embodiments discussed herein are directed generally to a fluid delivery system that is capable of delivering a large volume of a fluid, such as a fluid containing gene therapy ingredients, to a targeted tissue within a subject. The large volume of fluid may be delivered at a high pressure, and the fluid delivery system may be capable of monitoring the pressure at the syringe tip and at the targeted tissue. In some embodiments, the fluid delivery system may be able to quickly discover and respond to changes in pressure to ensure proper delivery of fluid to the targeted tissue.

FIG. 1 depicts external features of a fluid delivery system, generally designated 100, according to an embodiment. In various embodiments, the fluid delivery system 100 may generally include an injector body 105, a display or a graphical user interface ("GUI") 115, and a base unit that may enclose, among other things, a computing device 120. In certain embodiments, the fluid delivery system 100 may further include one or more switches, human interface devices, controls, and/or the like, such as, for example, a foot switch, a hand switch, keyboards, pointing devices, and/or the like for operating various components of the system. In some embodiments, the fluid delivery system 100 and/or the components thereof may be configured to be portable and/or movable. Thus, the fluid delivery system 100 may include any number of wheels, casters, extension arms, rotating portions, height adjustable portions, and/or the like. While the current description discloses all of the elements herein as being connected as a single unit, those skilled in the art will recognize that any of the components mentioned herein may be separate and/or remotely connected to the other components without departing from the scope of the present disclosure.

Figure 2:
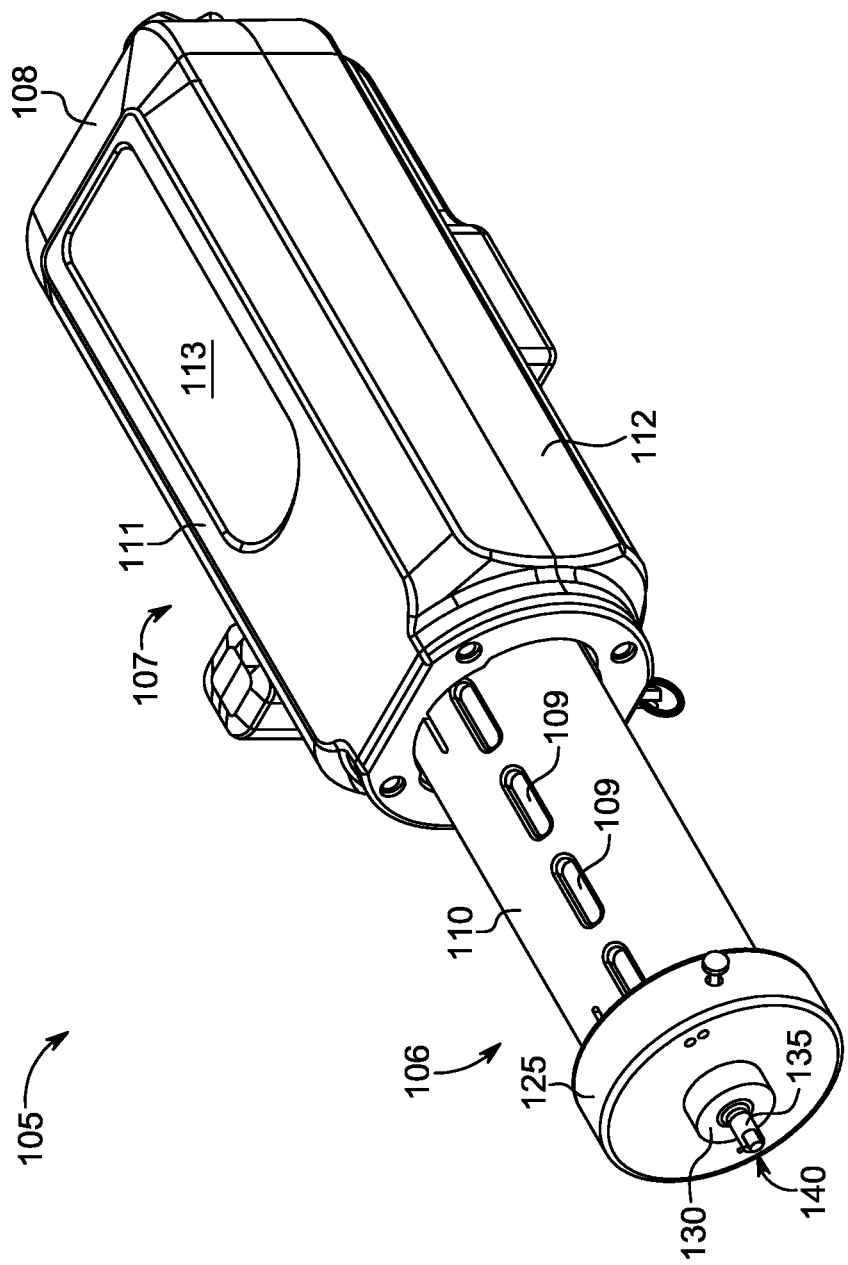
FIG. 2 depicts a perspective view of external components of an injector head according to an embodiment.

In various embodiments, the injector body 105 may be configured as illustrated in FIG. 2. Generally, the injector body 105 may include at least an injector 107 and a syringe assembly 106. The injector 107 may generally be configured to provide a force upon the syringe assembly 106 to effectuate distribution of the contents of the syringe assembly, as discussed in greater detail herein. In some embodiments, the injector 107 may be configured to drive a pump such as, for example, a piston pump, a reciprocating pump, a rotational pump, a gear pump, a peristaltic pump, a diaphragm pump, or the like.

In some embodiments, the injector 107 may include a housing 108. The housing 108 may include one or more enclosure pieces 111, 112 and one or more access panels 113, which may allow a user to access portions of the injector 107 covered by the housing or allow for improved access to exposed portions of the injector. In further embodiments, the housing 108 may include hinged or slidable access panels 113 for accessing motors or pumps for moving fluid through the delivery tubing and/or accessing ports for connecting, for example, a power cord, a controller, a computer, a memory device, a display, a hand switch or footswitch, or various combinations thereof. In other embodiments, the housing 108 may be removably attached to a frame and may be removed to allow access to components such as motors, pumps, syringe holders, tubing management systems without the need for an additional access panel 113.

In various embodiments, the syringe assembly 106 may generally include a pressure jacket 110, an endplate 125, a securing device 130, and an end plug 135. The end plug 135 may include an opening 140 to allow fluid to pass therethrough. In some embodiments, the pressure jacket 110 may enclose a syringe body therein, as discussed in greater detail herein. In some embodiments, the pressure jacket 110 may be configured to attach the syringe assembly 106 to the injector 107 through the use of an attachment mechanism, as described in greater detail herein. In some embodiments, the pressure jacket 110 may include one or more openings 109, such as slots, windows, or the like, for viewing the fluid contained in the syringe body. In some embodiments, the pressure jacket 110 may include any number of marks and/or the like to assist a user in assembling the pressure jacket to the various other components depicted herein, for determining the amount of fluid within the syringe body, and/or the like.

Figure 3A:
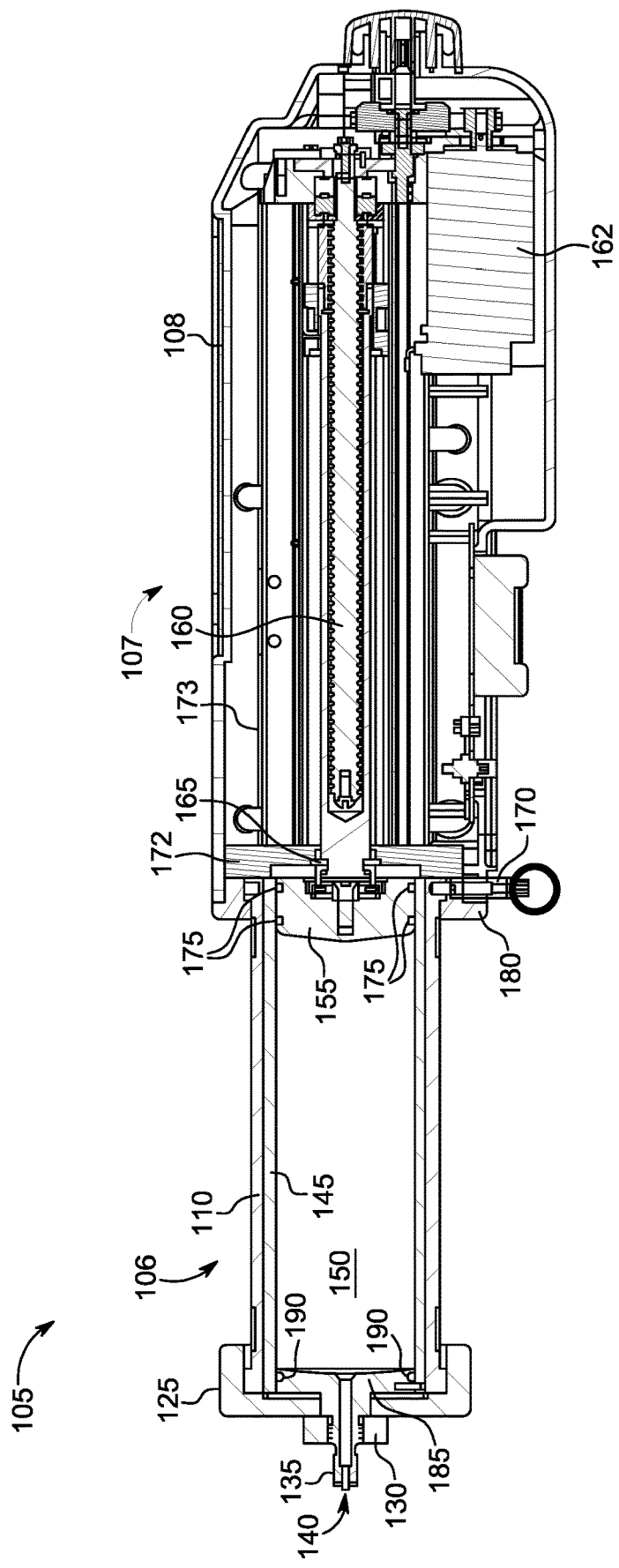
FIG. 3A depicts a first cross-sectional side view of an injector head and a syringe according to an embodiment.
Figure 3B:
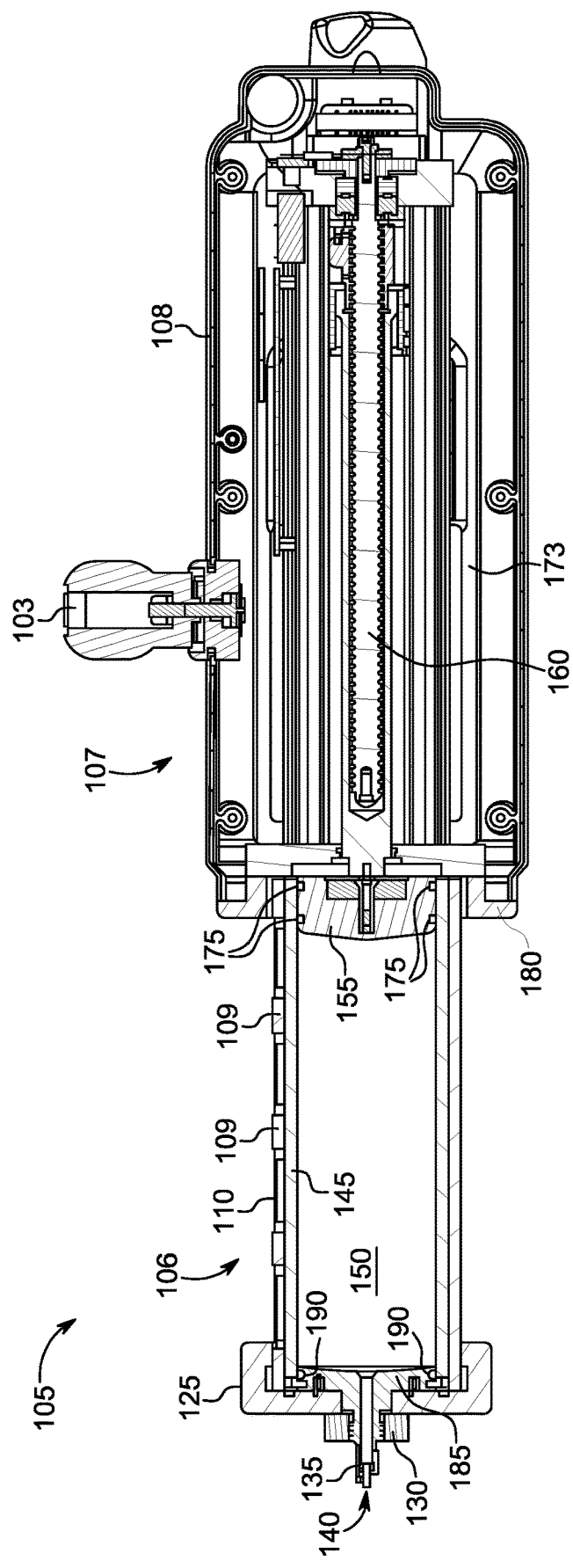
FIG. 3B depicts a second cross-sectional side view of an injector head and a syringe according to an embodiment.

FIGS. 3A and 3B depict cross-sectional side views of the injector body 105 according to an embodiment. In some embodiments, the injector 107 may provide a force to drive a plunger 155 in a substantially distal direction within a syringe body 145 to force fluid out of the syringe body. In some embodiments, the injector 107 may provide a force to drive the plunger 155 in a substantially proximal direction within a syringe body 145 to stop fluid from exiting the syringe body 145 and/or to draw fluid into the syringe body, as will be described in greater detail herein. In some embodiments, the injector 107 may be configured to control an injection according to a series of flow rate targets over a period of time and/or a series of pressure targets over a period of time.

Figure 4A:
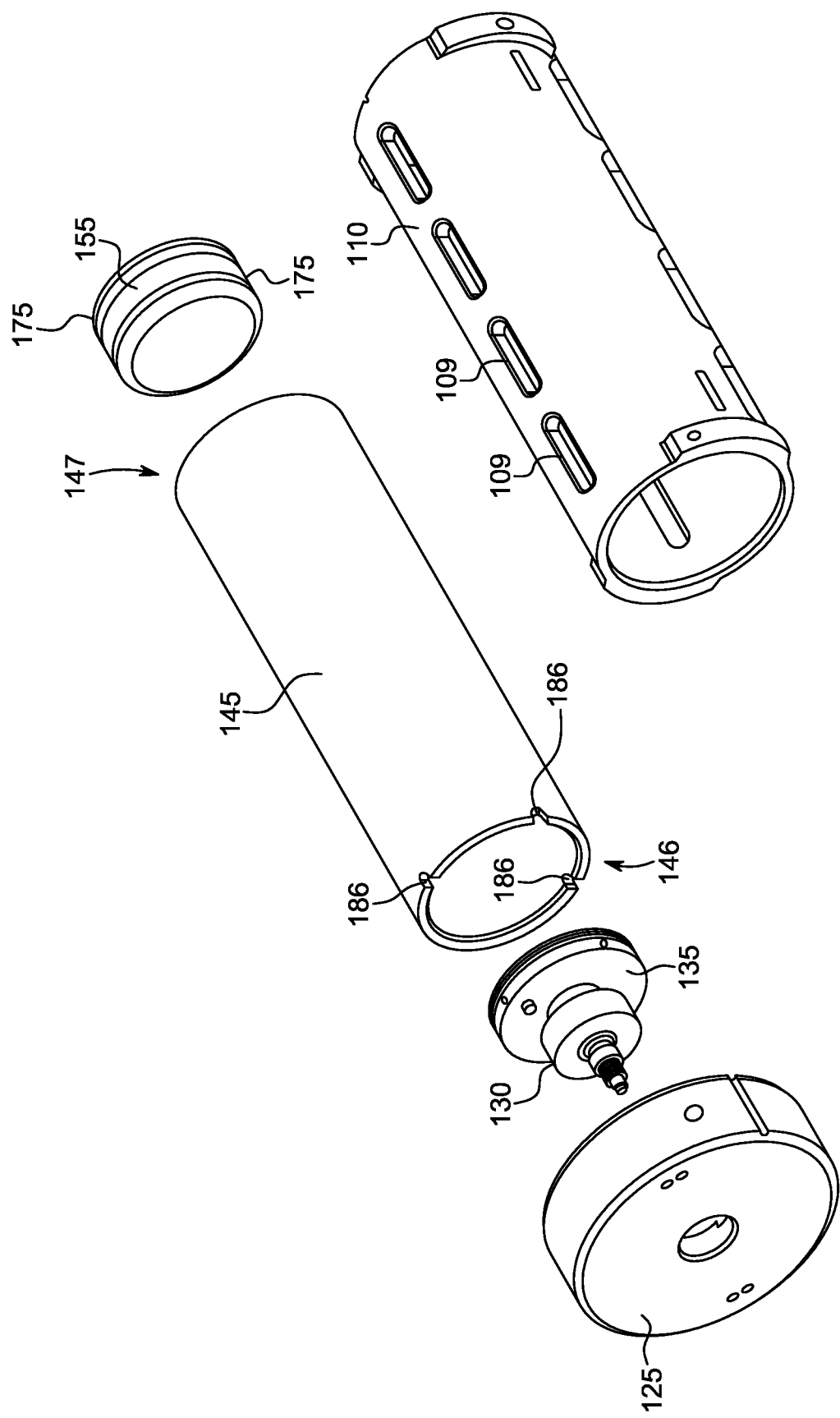
FIG. 4A depicts the various components of a syringe and a pressure jacket according to an embodiment.
Figure 4B:
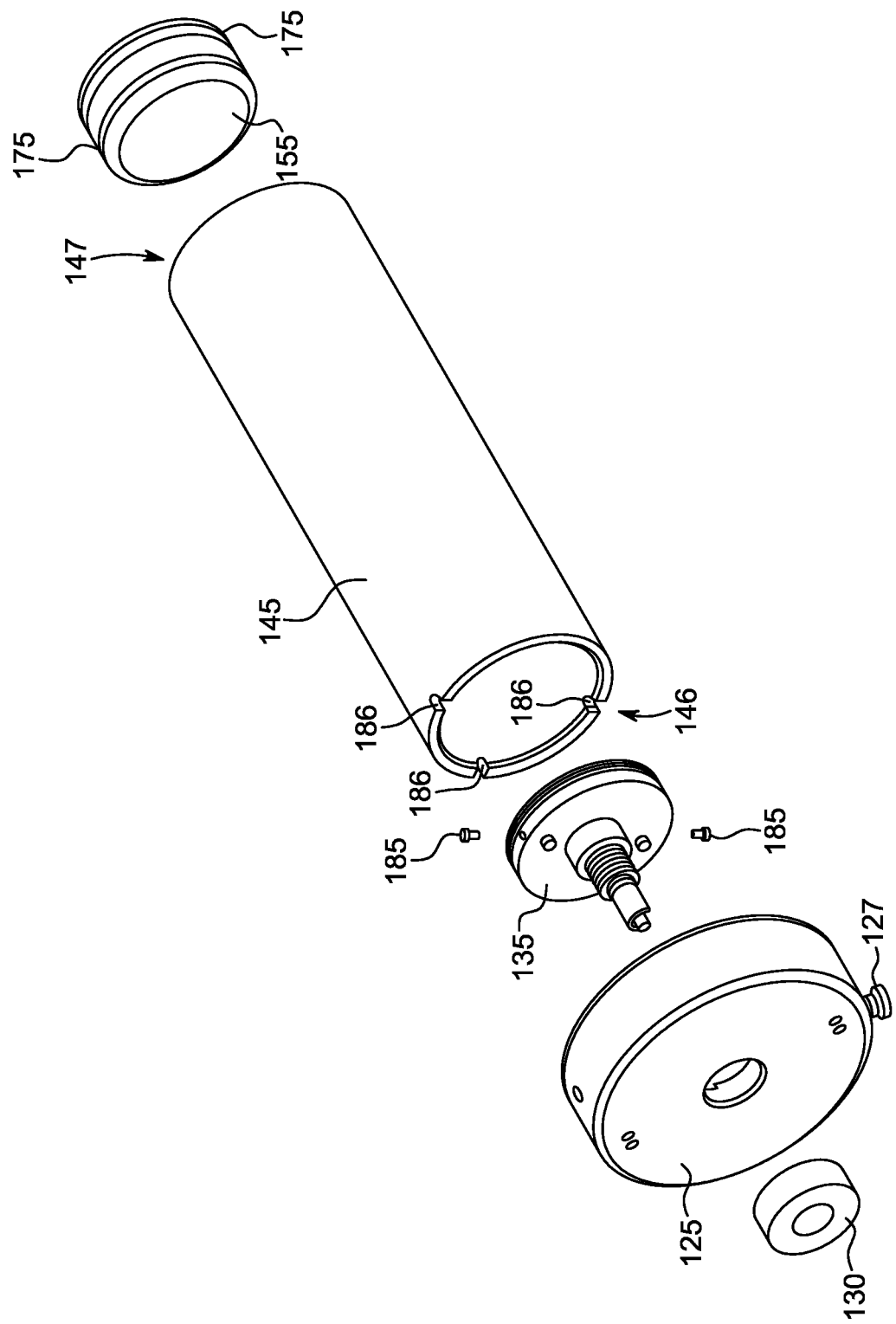
FIG. 4B depicts an alternate view of the various components of the syringe of FIG. 4A according to an embodiment.

As also depicted in FIGS. 4A and 4B, the pressure jacket 110 may enclose the syringe body 145 according to various embodiments. The syringe body 145 is not limited by this disclosure, and may generally be any syringe body, pump, or the like now known or later developed. Thus, while the term "syringe body" is primarily used herein, those skilled in the art may appreciate that the term may encompass any type of pump, particularly fluid pumps. Illustrative examples of syringe bodies may include, but are not limited to, a bladder syringe, a blow-molded syringe, a collapsible syringe, a rigid syringe, a balloon-type syringe, a flexible wall syringe, or the like. In some embodiments, the syringe body 145 may be configured to float or move freely within the pressure jacket 110 without affecting its volume accuracy, but may be sufficiently secured to prevent excessive movement within the pressure jacket. In some embodiments, the syringe body 145 may define a fluid delivery volume therein 150. The fluid delivery volume 150 may be configured to house a sufficient volume of fluid to effect delivery to a subject as described herein. In certain embodiments, the fluid volume may be about 10 ml to about 2000 ml. Specific examples of fluid volumes may be about 10 ml, about 25 ml, about 50 ml, about 100 ml, about 200 ml, about 250 ml, about 500 ml, about 750 ml, about 1000 ml, about 2000 ml or any value or range between any two of these values. In some embodiments, the fluid volume may be greater than 2000 ml. In some embodiments, the syringe volume may be different than the fluid volume. In particular embodiments, the syringe volume may be larger than the fluid volume. Thus, in some embodiments, the syringe volume may be about 10 ml to about 2000 ml. Specific examples of syringe volumes may be about 10 ml, about 25 ml, about 50 ml, about 100 ml, about 200 ml, about 250 ml, about 500 ml, about 750 ml, about 1000 ml, about 2000 ml, or any value or range between any two of these values. In some embodiments, the syringe volume may be greater than 2000 ml. In some embodiments, the syringe body 145 may incorporate a pump system that is attached to a large volume of fluid to allow an injected to be very small or vary large and/or adjustable during the procedure.

In various embodiments, the syringe body 145 may be constructed out of a material that is capable of withstanding a fluid pressure of about 10 psi to about 2000 psi. Specific examples of pressures may include about 10 psi, about 25 psi, about 50 psi, about 100 psi, about 250 psi, about 500 psi, about 750 psi, about 1000 psi, about 1500 psi, about 2000 psi, or any value or range between any two of these values. In some embodiments, the syringe body 145 by itself may not be capable of withstanding the fluid pressure, but when accompanied by the pressure jacket 110 described herein, the syringe body may be able to withstand the fluid pressure. In some embodiments, the syringe body 145 may generally be constructed of materials that do not alter or react with the contents of the syringe body. In some embodiments, the syringe body 145 may be of uniform construction with little or no imperfections on any surface of the syringe body and/or any pump components, particularly imperfections that may trap air, cells, fluid, or other components within. In particular embodiments, the syringe body 145 may be cylindrical in shape where the inside radius of the syringe body is uniform throughout its length, such as, for example, a single hollow tube. In some embodiments, the syringe body 145 may be machined as a single piece. In other embodiments, the syringe body 145 may be molded as a single piece. In some embodiments, use of a single hollow tube for the syringe body 145 may allow for the tube to be extruded or machined to a tighter tolerance for the radius of the syringe body. Illustrative examples of a tight tolerance that are acceptable may include about 0.001 inches to about 0.009 inches. Particular examples may include about 0.001 inches, about 0.002 inches, about 0.003 inches, about 0.005 inches, about 0.007 inches, about 0.009 inches, or any value or range between any two of these values. In some embodiments, the syringe body 145 may be constructed of a disposable material. In other embodiments, the syringe body 145 may be constructed of a reusable material so that the syringe body can be refilled for subsequent use. In some embodiments, the syringe body 145 may be constructed of polycarbonate, polyethyleneterephthalate (PET), cyclic olefin polymer, polypropylene, polystyrene, polyvinylidene chloride (PVDC), polyethylene napthalate (PEN), high-density polyethylene (HDPE), polypropylene, nylon, glass, glass-containing compounds, glass-like compounds, and/or the like.

In some embodiments, the syringe body 145 may include a distal end 146 and a proximal end 147. The distal end 146 of the syringe body 145 may be configured to receive the end plug 135 to form a seal with the inside surface of the syringe body by means of a first seal 190. In some embodiments, the first seal 190 may be a separate component from the end plug 135, such as, for example, an added O-ring and/or the like. In these embodiments, the first seal 190 may be fixedly attached to the end plug 135 by any means of attachment, including attachment apparatuses, adhesives, and/or the like, or the first seal may be removably attached to the end plug. In other embodiments, the first seal 190 may be fabricated as a portion of the end plug 135. In some embodiments, the end plug 135 may be fabricated as a single solid piece with an opening 140 therethrough to ensure that fluid can only travel through the opening, and that no amount of fluid may become trapped in pockets or imperfections within the end plug. The end plug 135 may be constructed of any material that does not interact with the fluid and is capable of withstanding fluid pressures as described herein. In some embodiments, the end plug 135 may be constructed of a disposable material. In other embodiments, the end plug 135 may be constructed of a reusable material.

In some embodiments, the end plug 135 may be secured to the syringe body 145 by means of one or more attachment devices 185. The one or more attachment devices 185 are not limited by this disclosure and may generally be any means of providing a secure connection of the end plug 135 to the syringe body 145. Specific examples of attachment devices 185 may include clips, fasteners, screws, rivets, and/or the like. In some embodiments, the one or more attachment devices 185 may be fabricated as a part of the end plug 135. In some embodiments, the one or more attachment devices 185 may be fabricated as part of the syringe body 145. In yet other embodiments, the one or more attachment devices 185 may be standalone attachment devices that are not fabricated as a portion of either the syringe body 145 or the end plug 135. In embodiments where the attachment devices 185 are fabricated as standalone devices or as a part of the end plug 135, the distal end 146 may include one or more clearance slots 186 that may be configured to receive the attachment devices and ensure a secure attachment.

In various embodiments, the syringe body 145 may be configured to receive a plunger 155 therein. In some embodiments, the plunger 155 may form a seal against the interior of the syringe body 145 by means of one or more second seals 175. In some embodiments, the second seals 175 may be a separate component from the plunger 155, such as, for example, added 0-rings and/or the like. In these embodiments, the second seals 175 may be fixedly attached to the plunger 155 by any means of attachment, including attachment apparatuses, adhesives, and/or the like, or the second seals may be removably attached to the first plunger. In other embodiments, the second seals 175 may be fabricated as a portion of the plunger 155. In various embodiments, the second seals 175 may be fabricated of any material commonly known for use in providing a seal from liquids, particularly pressurized liquids. Specific examples may include rubber, ethylene propylene diene monomer rubber (EPDM rubber), thermoplastic elastomers, polymers, and/or the like. In various embodiments, the plunger 155 may be fabricated of a disposable material. In other embodiments, the plunger 155 may be fabricated of a reusable material. The type of material is not limited by this disclosure, and may generally be any material now known or later developed for use in syringe plungers.

In some embodiments, the plunger 155 may be configured to slidably move in a distal and/or a proximal direction within the syringe body 145, as described in greater detail herein. In some embodiments, the plunger 155 may be precisely located so that the location of the plunger corresponds to an exact amount of fluid located within the fluid delivery volume 150. For example, in some embodiments, movement of the plunger 155 in a distal direction of 0.009 inches may cause 1 ml of fluid to be expelled from the fluid delivery volume 150.

In various embodiments, the pressure jacket 110 may be configured to slidably move in relation to the syringe body 145 to encapsulate the syringe body therein. The pressure jacket 110 may further be configured to provide a stable means of encapsulating the syringe body 145 to prevent excessive movement of the syringe body, expansion of the syringe body, destruction of the syringe body, and/or the like. By providing a stable means of encapsulating the syringe body 145, the pressure jacket 110 may act to ensure an accurate pressure, fluid delivery, and volume of fluid within the syringe body at all times, as described in greater detail herein. In some embodiments, the pressure jacket 110 may be securably positioned around the syringe body 145 by means of the endplate 125 and/or the securing device 130. In particular embodiments, the endplate 125 may contain an opening to allow a distal end of the end plug 135 to extend therethrough. Accordingly, the securing device 130 may be secured around the distal end of the end plug 135 to secure the endplate 125 to the pressure jacket 110. For example, the distal end of the end plug 135 may contain a plurality of threads so that the securing device 130 may act as a nut or the like and can be screwed onto the end plug. In some embodiments, the endplate 125 may be affixed to the end plug 135 and the pressure jacket 110 in such a manner that the pressure jacket is releasably secured to the injector head and also constrains the syringe body 145, while still allowing some minimal movement of the syringe body. Thus, in these embodiments, the pressure jacket 110 may be securely connected to the endplate 125.

Referring to FIGS. 3A-3B and FIGS. 5A-5D, the injector 107 may include one or more driving devices 162 according to various embodiments. The driving devices 162 may include motors or the like. In some embodiments, the driving devices 162 may be configured to apply a moving force to at least a portion of the syringe body 145 or components thereof. The driving devices 162 may be attached to the housing 108 (FIG. 2) or a frame provided under the housing which maintains the position of the driving devices during use or the fluid delivery system 100. In some embodiments, the driving devices 162 may have a syringe actuation component 160, such as a piston. The actuation component 160 may include a connector that can be configured to connect to the plunger 155 and allow the motor to advance or retract the plunger in the syringe body 145. In certain embodiments, the actuation component 160 may include a piston that contacts the plunger 155 and is capable of advancing the plunger, but not retracting the plunger. In some embodiments, the actuation component 160 may include one or more sensors (not shown) positioned to contact the plunger 155 before or during actuation. Thus, in such embodiments, the driving devices 162 may effectuate discharge of the fluid only. In other embodiments, the actuation component 160 may include a piston that contacts the plunger 155 and locks into place via a removable locking mechanism 165. The removable locking mechanism 165 may allow for attachment and detachment of the plunger 155 from the actuation component 160 so that various plungers and/or syringe assemblies may be used with the same injector 107, such as, for example, disposable syringe assemblies. The removable locking mechanism 165 is not limited by this disclosure, and may include any removable locking mechanisms now known or later developed, particularly those used for attachment and removal of various syringe components.

In various embodiments, the injector 107 may include a syringe mounting mechanism 172. In some embodiments, the syringe mounting mechanism 172 may generally be configured to mount or hold the syringe assembly 106 to the injector 107. Embodiments are not limited to any particular syringe mounting mechanism. For example, in some embodiments, the syringe mounting mechanism 172 may be a device configured to accept and hold a syringe or vial holding fluid by removably attaching to the syringe or vial body or flanges associated with the syringe or vial. In other embodiments, the syringe mounting mechanism 172 may be configured to accept and hold a secondary device housing a syringe or vial including a fluid, such as, for example, the pressure jacket 110 and/or a pressure jacket flange 180. In some embodiments, a securing pin 170 may provide an additional or alternative method of securing the syringe assembly 106 to the injector 107.

Figure 5A:
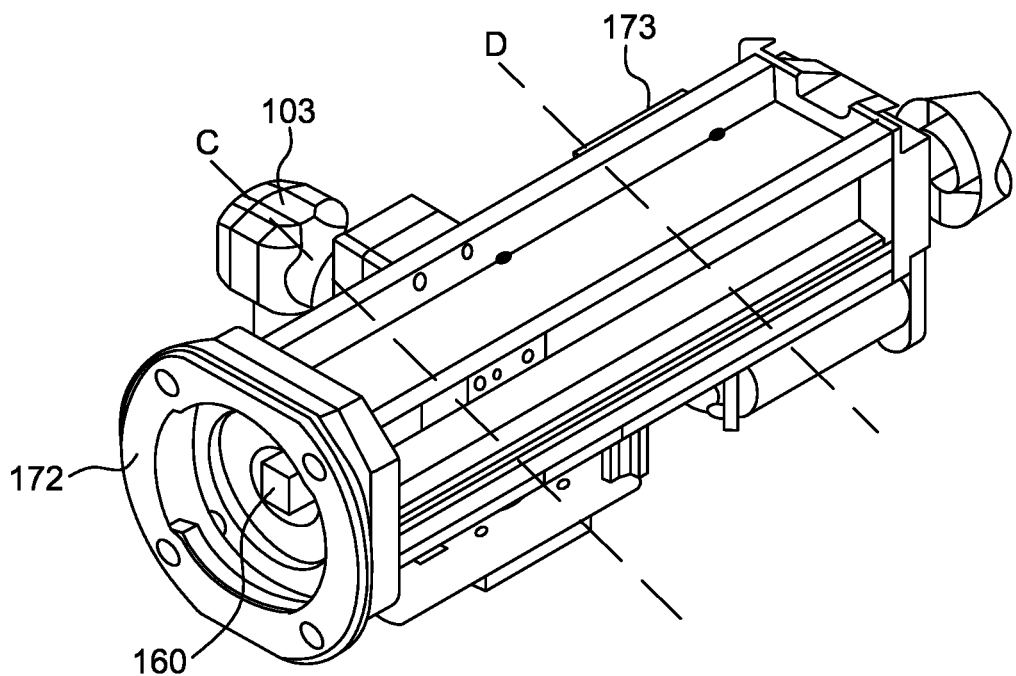
FIGS. 5A and 5B depict a perspective view of various internal components of the injector head according to an embodiment.
Figure 5B:
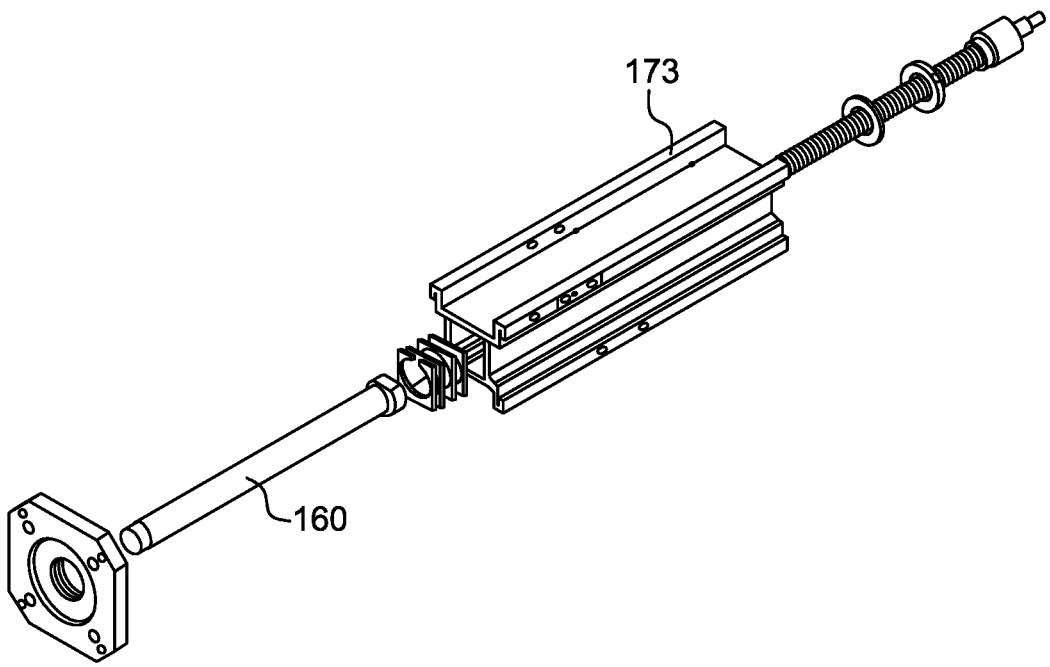
Figure 5C:
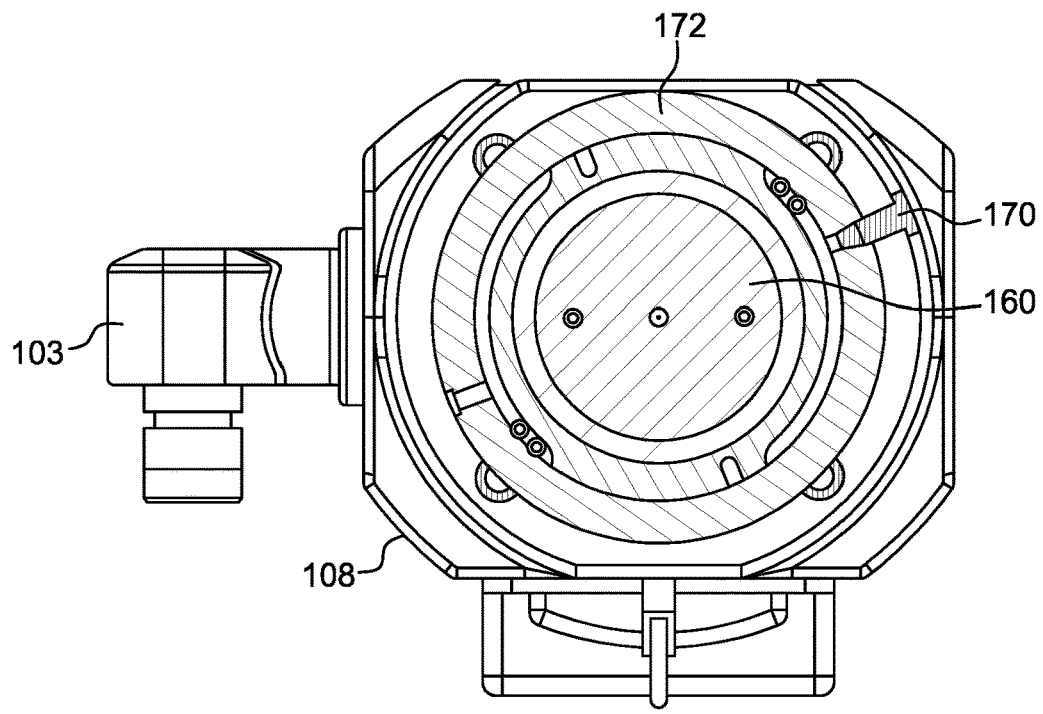
FIG. 5C depicts a cross sectional view of the injector head across line C of FIG. 5A according to an embodiment.
Figure 5D:
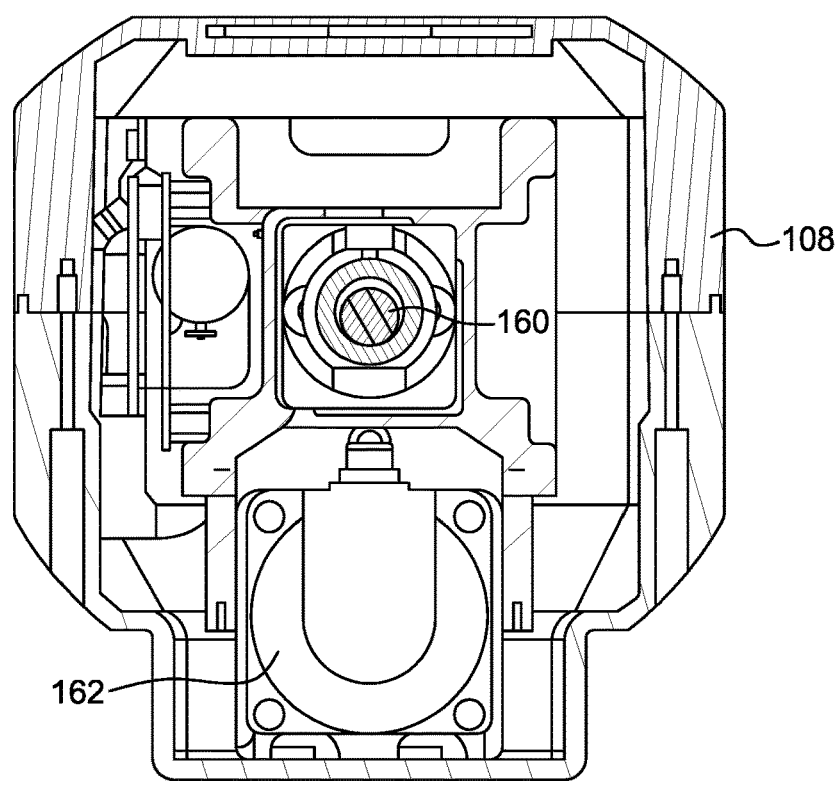
FIG. 5D depicts a cross sectional view of the injector head across line D of FIG. 5A according to an embodiment.

In various embodiments, the syringe mounting mechanism 172 may be associated with and attached to a framework 173 underlying the housing 108 rather than the housing itself. An example of such a framework 173 is provided in FIGS. 5A and 5B showing various perspectives of the framework. The framework 173 may generally be constructed of a rigid material that provides mechanical support for the syringe mounting mechanism 172 and/or the actuation component 160. In some embodiments, the framework 173 may substantially improve the accuracy and reproducibility of injections by reducing or eliminating flexion that can occur when the syringe mounting mechanism 172 and/or the actuation component 160 are attached to a housing 108 composed of a more flexible material. In some embodiments, the framework 173 may be composed of steel, aluminum, another metal or metal alloy, or a high tensile strength polymer compositions. In some embodiments, the framework 173 may be designed to fit within the housing 108 and provide attachment sites for mechanical components of the injector 107 in addition to the syringe mounting mechanism 173 and/or actuation component 160.

In various embodiments, the injector 107 may include an injector mounting mechanism 103. In some embodiments, the injector mounting mechanism 103 may generally be configured to mount or hold the injector 107 to the fluid delivery system 100. Embodiments are not limited to any particular injector mounting mechanism. For example, in some embodiments, the injector mounting mechanism 103 may be a device configured to accept an arm or the like of the fluid delivery system 100, where the injector mounting mechanism contains any means of securing the injector to the arm. In some embodiments, the injector mounting mechanism 103 may be configured to allow the injector 107 to rotatably pivot about one or more axes to be positioned in any manner that may be desired by a user. In some embodiments, the injector mounting mechanism 103 may be associated with, or attached to, the framework 173. In other embodiments, the injector mounting mechanism 103 may be attached to the housing 108.

Figure 6:
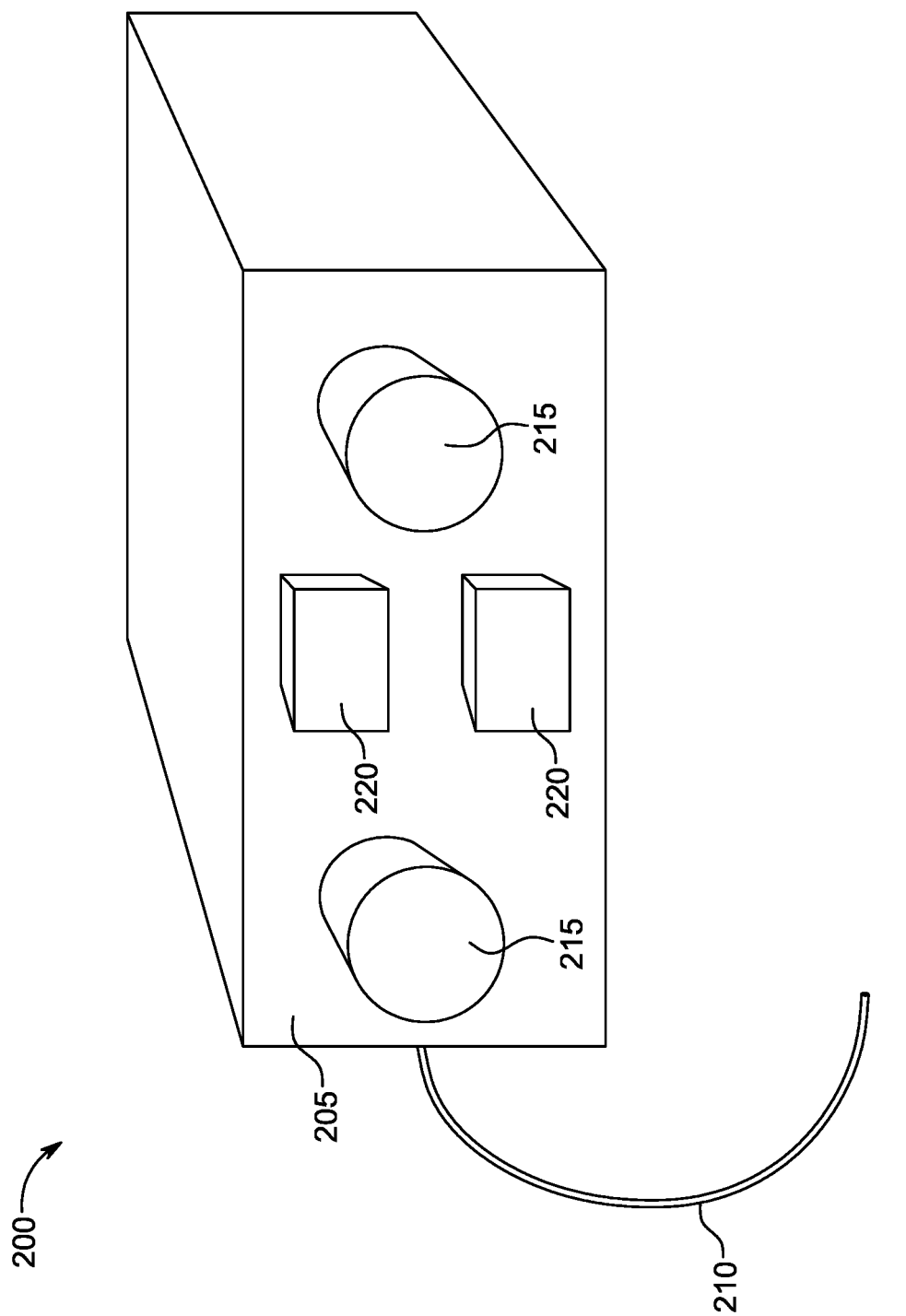
FIG. 6 depicts an intracorporeal sensing unit according to an embodiment.

As depicted in FIG. 6, the fluid delivery system 100 may include one or more intracorporeal sensing systems, generally designated 200, according to various embodiments. The intracorporeal sensing systems 200 may generally have a control module 205 and a sensor 210. In some embodiments, the control module 205 may be configured to be an integrated component of the computing device 120 (FIG. 1). In other embodiments, the control module 205 may be a standalone component that is in operative communication with the computing device 120 (FIG. 1), such as by wireless or hardwire communication. In some embodiments, the control module 205 may receive one or more signals from the sensor 210. The control module 205 may optionally interpret the signals as pressure readings, and may transmit the pressure readings to the computing device 120 (FIG. 1).

In various embodiments, the control module 205 may include one or more controls 215, one or more communications ports 220, and/or one or more displays (not shown). The one or more controls may be used to control the sensor 210, such as, for example, turning the sensor on or off, determining what feedback parameters the sensor senses, directing the sensor to the targeted tissue, and/or the like. The one or more communications ports 220 may allow the control module 205 to communicate with the computing device 120 (FIG. 1), as previously described herein. In some embodiments, when the control module 205 is connected to the computing device 120 (FIG. 1) via the one or more communications ports 220, the computing device may remotely control the control module, thereby deactivating the one or more controls 215.

In various embodiments, the sensor 210 may be delivered to the targeted tissue for sensing the pressure at the targeted tissue before, during, and after delivery of fluid from the syringe assembly 106 (FIG. 2). The sensor 210 may generally be configured to continuously monitor one or more feedback parameters at the location of the targeted tissue and quickly transmit signals to the control module 205 indicating the sensed feedback parameters. Illustrative examples of feedback parameters may include, but are not limited to, pressure in a receiving vessel, pressure in the targeted tissue, temperature, pH, physiological status, an image property, a tissue stretch property, a tissue conductivity, a tissue ultrasound property, a flow rate in the targeted tissue, a fluid cell count, a fluid particle count, a density of a measurable tracer, and the like. Accordingly, in some embodiments, the sensor 210 may be constructed of components that allow for quick transmission of pressure signals. Specific examples of components that may allow for quick transmission of signals may include fiber optic components, wireless radio components, and/or the like. The sensor 210 is not limited by this disclosure in the components and/or methods used for sensing. Thus, any sensing devices now known or later developed may be used to sense as described herein. In some embodiments, the sensor 210 may be connected via a wired connection to the control module 205, and may be distributed into the subject via a cannula or the like. In other embodiments, the sensor 210 may be connected via a wireless connection to the control module 205, and thus may be distributed into the subject via injection, oral ingestion, intranasal ingestion, and/or the like. In these embodiments, the wireless connection may be encrypted or otherwise protected by any method now known or later developed to ensure a secure connection between the sensor 210 and the control module 205.

Referring back to FIG. 2, in various embodiments, the fluid delivery system 100 may include delivery tubing for transferring the fluid from the syringe assembly 106 to a delivery port and/or the like (not shown) configured to allow injection of the fluid into a subject. In some embodiments, the delivery port may be a port at or near a point of entry on the body of a subject. The delivery tubing may include a tubing extension of any length extending from a syringe connector (such as, for example, the end plug 135) to the delivery port. In some embodiments, the tubing may include intervening tubing sections that act as extensions or perform specialized functions. The tubing extension may generally be of sufficient length to extend from the syringe to the subject to whom the fluid is to be delivered. Thus, the tubing extension may have length of from about 5 in to about 50 in, and in particular embodiments, the tubing extension may have a length of from about 10 in to about 50 in, about 15 in to about 45 in, about 20 in to about 40 in, or about 20 in to about 35 in. In certain embodiments, the tubing extension may have a length of 20 in, 36 in, or 48 in. Tubing extensions of such lengths may be configured to be accepted by a tubing management system while providing sufficient length to allow user maneuverability during the fluid delivery procedure.

The tubing extensions of various embodiments may include one or more connectors on each end, and the connector may be any connector known in the art. For example, a syringe connector may be mounted on an end of the tubing extension configured to be attached to the syringe and may be, for example, a luer or swabable luer type connector. The end of the tubing extension opposite the syringe connector may be configured to attach to a needle or other delivery device and may be a luer or swabable luer type connector. In other embodiments, the end of the tubing extension opposite the syringe connector may be configured as a tubing connector such that the tubing connector may attach to intervening tubing sections. In various embodiments, the tubing connector may be a luer connector. In some embodiments, the tubing may include a communication transmission capability In various embodiments, the communication transmission capability may be wired or wireless, and may include any number of wires, fiber optic cables, wireless radios, or other means to allow information to be passed from the targeted tissue.

In various embodiments, the fluid delivery system 100 may include any number of cords for powering the system using standard AC outlets. In some embodiments, the fluid delivery system 100 may include an isolation transformer (not shown). The isolation transformer may generally transfer electrical power from the AC power source to the various components of the fluid delivery system 100. In some embodiments, the isolation transformer may isolate the various components from the electrical power source to prevent system damage from spikes in electrical activity. In some embodiments, the isolation transformer may allow for non-medical-grade components to be used in conjunction with, or in place of, the various components described herein. Non-medical-grade components may contain leakage currents that are below an approved level, but the leakage currents may be limited by the isolation transformer when used as described herein. In some embodiments, the fluid delivery system 100 may include a battery configured to power the system controller in the event that the system is disconnected from an AC power source. In some embodiments, the battery may be charged while the fluid delivery system 100 is connected to an AC power source.

In various embodiments, the fluid delivery system 100 may include a system monitor device (not shown). The system monitor device may act as an independent monitoring device that functions separately from the computing device 120. In some embodiments, the system monitor device may be physically and/or electrically independent from the computing device 120. In some embodiments, the system monitor device may act to shut down and/or disable the fluid delivery system 100 in the event that an unsafe condition is sensed. Unsafe conditions are not limited by this disclosure, but may include, for example, unsafe environmental conditions, unsafe equipment installation, power failure, unsafe biological conditions within the subject, and/or the like.

As provided in FIG. 1, the fluid delivery system 100 of some embodiments may include a display 115. Such a display 115 may be a color display or a black and white display. In some embodiments, the display 115 may be configured to allow a user to program or otherwise operate the fluid delivery system 100. In some embodiments, the display 115 may display real-time data with regard to the operation of the fluid delivery system 100. For example, in certain embodiments, the display 115 may have touchscreen capabilities or be otherwise configured to allow a user to interact with the fluid delivery system 100 and, in particular, the computing device 120, by manipulating or touching the display. In other embodiments, the fluid delivery system 100 may include a keyboard, mouse, or other human input device configured to allow the user to program or otherwise operate the fluid delivery system. In still other embodiments, the display 115 may be included as part of a laptop, smartphone, or tablet computer that is electronically associated to the system by a hard wired or wireless network. The display 115 may be fixed to the injector body 105, and in other embodiments, the display may be positioned away from the fluid delivery system 100 and attached to the system by a hard wired or wireless network. Such displays 115 may be configured to be tilted or swiveled to allow the display to be positioned by an operator.

In some embodiments, the display 115 may be configured to present or provide data and information to an operator in an intelligible form or format, i.e., visually display this information and data in electronic form. In certain embodiments, the fluid delivery system 100 may include a printer 332 (FIG. 7) which may be configured to physically display this information and data in print form. The printer 332 (FIG. 7) of various embodiments may be of any type and includes off the shelf ink-jet and laser printers. In particular embodiments, the printer 332 (FIG. 7) may be configured to print adhesive backed labels. In still other embodiments, the fluid delivery system 100 may include a speaker 334 (FIG. 7) to audibly present this information and data in audible form. For example, a speaker may be configured to produce an audible "beep" when an injection is complete, or when the fluid has been used up or is nearly used up. In various embodiments, such devices may be in communication with the computing device 120 or other computing device through output interfaces.

Figure 7:
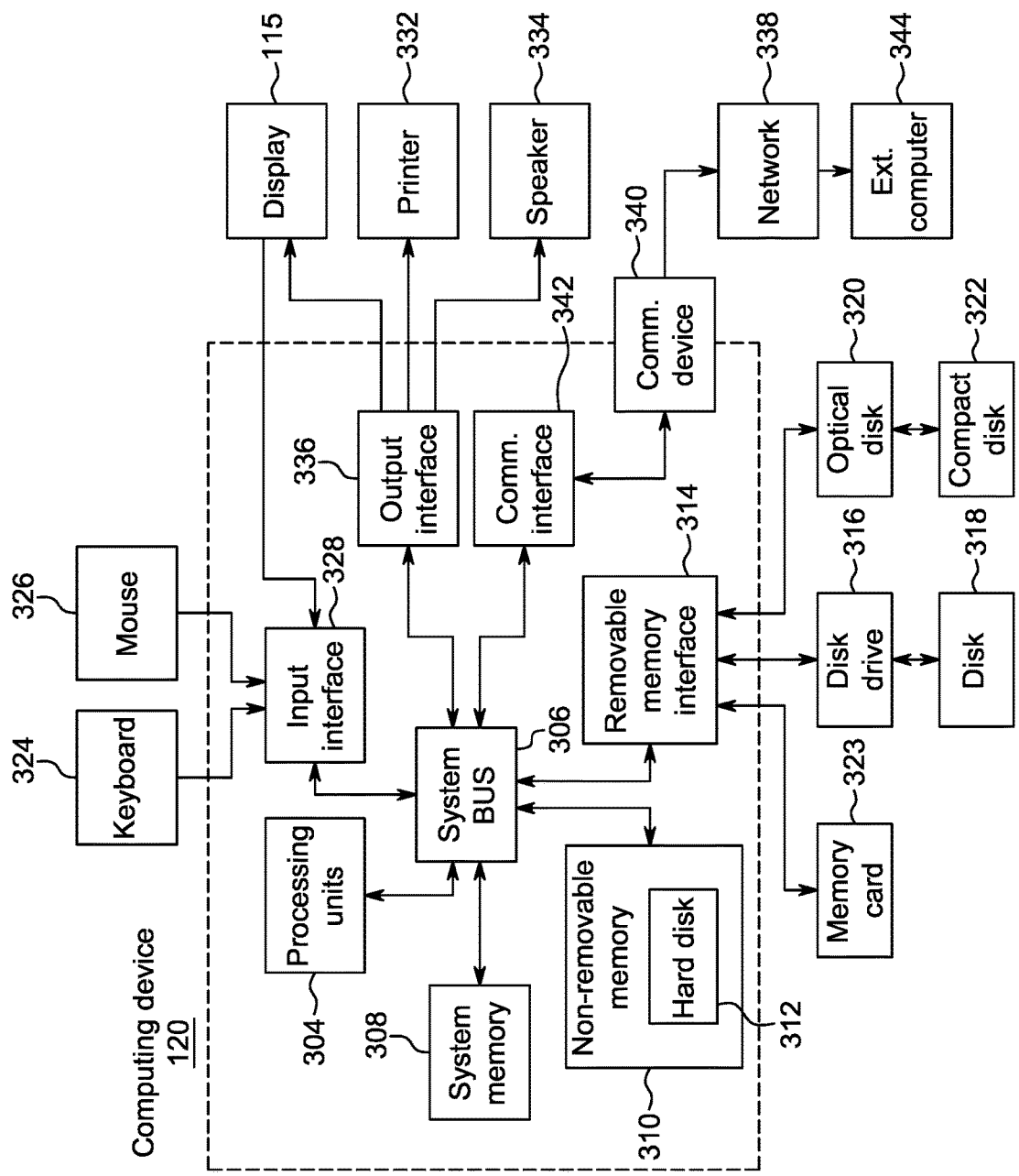
FIG. 7 depicts a schematic block diagram of various components of a computing device according to an embodiment.

Referring to FIG. 7, in various embodiments, the computing device 120 may include one or more components for completing various operations as described herein, for execution of code, and/or for creation and communication of data. In some embodiments, the computing device 120 and its various components described herein may be distributed throughout the fluid delivery system 100 (FIG. 1) For example, some components may reside in the display unit 115, the injector head 105, and/or the base unit. The computing device 120 may include one or more processing units 304 (typically referred to as a central processing unit or CPU) that serve to execute computer-based instructions received in an appropriate data form and format. Further, the processing units 304 may be in the form of multiple processors executing code in series, in parallel, or in any other manner for appropriate implementation of the computer-based instructions. As used herein, the computing device 120 may be operably configured to execute appropriate software to perform and implement the processing steps of the methods and systems disclosed herein. The computing device 120 may have a computer-readable storage medium capable of storing computer-readable program code or instructions that cause the processing units 304 to execute, configure, or otherwise implement the methods, processes, and transformational data manipulations discussed herein. Still further, the computing device 120 may be in the form of a personal computer coupled to the fluid delivery system 100, a processor formed integrally with the fluid delivery system, a computer provided remotely from the fluid delivery system, or any other type of computing device having the necessary processing hardware to appropriately process data to effectively implement the processes described herein. Illustrative examples may include, but are not limited to, a smartphone, a personal digital assistant (PDA), a tablet computing device, a phone-tablet hybrid (e.g., a "phablet"), a laptop computer, a netbook, an ultrabook, a desktop computing system, and/or the like.

The computing device 120 may further include a system bus 306 to facilitate appropriate data communication and processing information between the various components of the computing device. The system bus 306 may be any of several types of bus structures, including a memory bus or memory controller, a peripheral bus, or a local bus using any of a variety of bus architectures. In particular embodiments, the system bus 306 may facilitate data and information communication between the various components (whether internal or external to the computing device 120) through one or more interfaces.

In various embodiments, the computing device 120 may include system memory 308 with computer storage media such as volatile and non-volatile memory, ROM, and/or RAM. A basic input/output system (BIOS) with appropriate computer-based routines may assist in transferring information between components within the computing device 120 and can be stored in ROM. The RAM portion of the system memory 308 may typically contain data and program modules that are immediately accessible to or presently being operated on by the processing units 304 such as, for example, an operating system, one or more application programming interfaces, application programs, program modules, program data, and other instruction-based computer-readable code.

The computing device 120 may also include other removable or non-removable, volatile or non-volatile computer storage media products. For example, the computing device 120 may include a non-removable memory 310 that communicates with and controls a hard disk drive 312, such as, for example, a non-removable, non-volatile magnetic medium. The computing device 120 may further include a removable, non-volatile memory interface 314 that communicates with and controls a magnetic disk drive unit 316 (which may read from and write to a removable, non-volatile magnetic disk 318), an optical disk drive unit 320 (which may read from and write to a removable, non-volatile optical disk, such as a CD ROM 322, a DVD disc, a Blu-Ray disc, and/or the like), a Universal Serial Bus (USB) port for use in connection with, for example, a removable memory card 323 and/or the like. Other removable or non-removable, volatile or non-volatile computer storage media may be used, including, but not limited to, magnetic tape cassettes, DVDs, digital video tape, solid state RAM, solid state ROM, and the like. These removable or non-removable, volatile or non-volatile magnetic media may be in communication with the processing unit 304 and other components of the computing device 120 via the system bus 306. The drives and their associated computer storage media may provide storage of operating systems, computer-readable instructions, application programs, data structures, program modules, program data, and other instruction-based computer-readable code for the computing device 120 (whether duplicative or not of the information and data in the system memory 308).

In some embodiments, the computing device 120 may include one or more discrete computer-readable media components or other media that can be accessed by the computing device, such as, for example, volatile media, non-volatile media, removable media, non-removable media, and the like. In certain embodiments, the computer-readable media may be stored in a non-transitory storage medium including, but not limited to, random access memory (RAM), read only memory (ROM), electrically erasable programmable read only memory (EEPROM), flash memory, or other memory technology, CD-ROM, digital versatile disks (DVDs), Blu-Ray discs, other optical disk storage, magnetic cassettes, magnetic tape, magnetic disk storage, other magnetic storage devices, or any other medium which may be used to store the desired information and which can be accessed by the computing device 120. In some embodiments, the computer-readable media may include communications media, such as computer-readable instructions, data structures, program modules, or other data in a modulated data signal such as a carrier wave or other transport mechanism. In other embodiments, the computer-readable media may include any information delivery media, wired media (such as a wired network and a direct-wired connection), and wireless media (such as acoustic signals, radio frequency signals, optical signals, infrared signals, biometric signals, bar code signals, etc.). Combinations of any of the above are also included within the scope of computer-readable media.

In various embodiments, the fluid delivery system 100 may be configured to allow a user to enter commands, information, and data into the computing device 120 using the touch-screen of the GUI display 115 via an operator input interface 328. In other embodiments, an operator may enter commands, information, and data into the computing device 120 using other attachable or operable input devices, such as a keyboard 324, a mouse 326, a remote control device, a microphone, a trackball, a joystick, a touchpad, a scanner, a tablet computer, and/or the like, via the operator input interface 328. Any arrangement that facilitates the input of data and information to the computing device 120 from an outside source may be used including, for example, a hard wired connection or an access via a wireless network device, such as Bluetooth, a wireless internet connection, a cellular connection, and/or the like. As discussed, these and other input devices are often connected to the processing unit 304 through the operator input interface 328 coupled to the system bus 306, but may be connected by other interface and bus structures, such as, for example, a parallel port, a game port, a USB port, and/or the like.

In some embodiments, the computing device 120 may operate in a network environment 338 through the use of a communications device 340, which may be either integrated with the computing device, or may be remotely accessed by the computing device. This communications device 340 may be operable by and in communication with the other components of the computing device 120 through a communications interface 342. Using such an arrangement, the computing device 120 may connect with or otherwise communicate with one or more remote computers, such as a remote computer 344 of an external information system, which may include some or all of the components described above in connection with the computing device 120. Using appropriate communications devices 340 such as, for example, a modem, a network interface, an adapter, a telephone line, a cable line, a fiber optic line, a T3 line, a cellular telephone connection, a Wi-Fi network, and/or the like, the computing device 120 may operate within and communicate through a local area network (LAN) and a wide area network (WAN), such as the network 338 shown in FIG. 7, but may also include other networks such as a virtual private network (VPN), an office network, an enterprise network, an intranet, the Internet, and/or the like. It may be appreciated that the network connections shown are exemplary and other means of establishing a communications link between the computers 120, 344 may be used.

Generally, the embodiments described herein may be configured to intelligently deliver a fluid that is sufficient for delivery to an average subject based upon models and calculations that may be programmed into the computing device 120, as described herein. In some embodiments, a user may input various parameters into the computing device 120 when the fluid is loaded into the fluid delivery system 100. Illustrative examples of the various parameters may include, but are not limited to, information about the subject to which the fluid is delivered, (i.e., height, weight, medical conditions, and the like), identification of the tissue and/or area to receive treatment, type of treatment to be delivered to the subject, measurements of the tissue and/or area to receive treatment, and/or the like. In some embodiments, the fluid delivery system 100 may be configured to determine the volume of fluid to be delivered, as well as an amount and/or concentration of gene therapy ingredients to be delivered, which may be based on the parameters received from the user. In some embodiments, the fluid delivery system 100 may be further configured to deliver a dose of fluid and/or gene therapy ingredients having a desired activity level based on the parameters received from the user. In some embodiments, the fluid delivery system 100 may be configured to deliver the fluid and/or gene therapy ingredients at a specified pressure, and may modify the pressure of delivery based upon feedback received from the intracorporeal sensing systems 200 (FIG. 6), as described herein.

In various embodiments, the computing device 120 may be configured to direct the injector body 105 (FIG. 1) to administer the fluid to a subject, monitor the pressure and rate of administration of the fluid delivery at the injector body, and receive feedback from the intracorporeal sensing systems 200 (FIG. 6). Based upon the feedback received, the computing device 100 may calculate any necessary changes to the pressure and rate of delivery and direct the injector body to adjust the pressure and rate of delivery accordingly. In particular embodiments, the computing device 120 may monitor the pressure and rate of administration of the fluid delivery at the end plug 135 (FIG. 2). Such embodiments may require one or more pressure sensors positioned at the end plug 135 (FIG. 2) and/or at other portions of the injector body 105 (FIG. 1) that are in communication with the computing device 120, such as through the communications interface 342 or the input interface 328. In other embodiments, the force on the plunger may be used to measure the pressure in the syringe. In yet other embodiments, the torque and/or the amperage of the one or more driving devices 162 (FIG. 3A) may be used to determine the pressure in the syringe.

In some embodiments, the computing device 120 may calculate any necessary changes to the pressure and rate of delivery using one or more algorithms that have been programmed based upon mathematical and/or physical models of the target tissue for an average subject. One such physical model that has been developed for determining pressure and flow of fluid is a dynamic anthropomorphic cardiovascular phantom disclosed in U.S. Patent Application Publication No. 2009/0226867 to Kalafut et al., the entire contents of which are incorporated herein by reference. Another physical model may be a liver model that may be used to mimic the pressure and flow response of fluid within a liver, particularly with regards to an injection of fluid into the liver model. By injecting fluid into the liver model and then observing the results of the injection, a researcher can devise an algorithm for the computing device 120 that corresponds to expected pressure and flow response in an actual liver when fluid is injected into a subject as described herein. While the above models refer to cardiac and hepatic tissue, those skilled in the art will recognize that any tissue may be used.

The fluid delivery system 100 may further be configured for priming (i.e., purging air from the tubing system) and delivering a fluid to a subject, as previously described herein. In addition, the fluid delivery system 100 may facilitate safe delivery of the fluid to multiple destinations, such as, for example, dose delivery to multiple tissue areas and/or multiple subjects.

The fluid delivery system 100 may be further configured to provide feedback information to a user. For example, in some embodiments, the fluid delivery system 100 may provide the user with information regarding the administration such as, but not limited to, the dosage of fluid delivered to the subject by mass (mg), volume (ml), dosing time (i.e., the time required for delivery), delivery time (i.e., the time of day), date, and/or fluid pressure in the delivery system during delivery. In some embodiments, the fluid delivery system 100 may reference subject data to determine the amount of fluid administered to the particular subject over time and provide a warning to the operator if the amount of fluid and/or the pressure of the fluid is too high or too low. In various embodiments, the information may be provided to the user in real time.

Following administration or the completion of an administration protocol, the fluid delivery system 100 may provide a summary of the procedure including any relevant data. For example, in various embodiments, the system may provide the dosage of fluid delivered to the subject by mass (mg), volume (ml), the amount of another pharmaceutical composition delivered to the subject (mg/ml), dosing time (i.e., the time required for delivery), delivery time (i.e., the time of day), date, and fluid pressure in the delivery system during delivery, and/or the like. Data may be provided either in real time during performance of the protocol and/or in summary form after completing. The data may be provided numerically and/or graphically. In certain embodiments, the display 115 may provide both numeric and graphic data simultaneously.

The fluid delivery system 100 may further provide subject identification and any critical data such as, weight, age, disease being treated or tested for, the procedure to be performed, the location of the injection/infusion site, and the like and various combinations thereof. Such data may be received at the time of or prior to the procedure. In certain embodiments, the operator may input a subject identification, and the fluid delivery system 100 may retrieve appropriate subject data from electronically archived records using a computer network or Internet connection. In still further embodiments, the fluid delivery system 100 may store subject information for more than one procedure.

Referring to FIGS. 1-7, in operation, the syringe body 145 may be loaded with any amount of a composition and the syringe body 145 may be installed into the injector 105. The plunger 155 may be specifically positioned so that the composition within the syringe body is a particular volume and pressure. The syringe actuation component 160 may be advanced to push the plunger 155 in a distal direction. The syringe actuation component 160 may be controlled by the computing device 120 to increase in speed, decrease in speed, stop, or reverse the plunger in the proximal direction depending on a desired pressure and or flow of the contents of the syringe body 145. Adjustments to the movement of the syringe actuation component 160 may be of any size (i.e., a large change in speed or a small change in speed) to ensure an exact volume and pressure is achieved. In some embodiments, the syringe actuation component 160 may first move the plunger 155 in a distal direction to displace blood in or around the tissue, and then increase the speed of the plunger movement to inject the fluid into the tissue.

User control of the fluid delivery system 100 may be carried out by any suitable means. For example, in some embodiments, a user may trigger delivery of the fluid using the GUI interface by pressing a button on the screen. In other embodiments, an external button may be used to trigger delivery. The external button may be configured to be activated, for example, by hand or using a foot pedal. In other embodiments, the delivery of the fluid may be coordinated with a physiological parameter, such as, for example, a heart phase, a vessel pressure, or a breath phase. In yet other embodiments, delivery may be triggered by the computing device 120. In further embodiments, the delivery may be triggered by a remote hand controller. In some embodiments, the fluid delivery system 100 may include an interrupt button that is configured to allow an operator to pause or abort an injection procedure in the event of, for example, subject discomfort or an emergency, while bypassing the GUI display 115, which also can be configured to allow the user to pause or abort an injection procedure. An interrupt button may be connected to LEDs and/or a printed circuit board to provide visual and/or auditory alarms when the interrupt button has been activated.

Various embodiments are directed to methods for using the fluid delivery system 100 and devices encompassed by the fluid delivery system. In some embodiments, before starting the injection procedure, the operator and/or the computing device 120 may determine the desired amount of fluid to be delivered to the subject based on the tissue to be treated, biological characteristics of the subject, and/or the like. The methods of various embodiments may include the step of inputting such information before beginning the procedure.

In certain embodiments, methods may further include generating a list of procedures to be performed over a time period. While the information provided in such a list may vary, in some embodiments, the list may include subject ID numbers, type of procedure, amount of fluid to be delivered to the identified subject, the time necessary of the procedure and/or a projected start time for the procedure, and the like. In particular embodiments, the information required for such a list may be received by the fluid delivery system 100 before initiation, and in other embodiments, information for the list may be provided before the initiation of the procedure for each individual subject. In still other embodiments, information for the list may be received from a remote location, and subject information may be provided to the system via an Internet or other network connection.

Initialization may include any number of steps necessary to prepare the system for delivery of a fluid. In some embodiments, initialization may include filling the system including all tubing and connectors with saline or another medical fluid to remove air from the fluid path, such as, for example, flushing the system. In some embodiments, the step of flushing the system may be carried out by manually filling various components with saline before connecting to the syringe. In other embodiments, the various components and/or various portions thereof may be prefilled with saline or another medical fluid before packaging.

In various embodiments, the method presented above may further include the step of delivering the fluid to the subject. Delivering the fluid may include the steps of inserting a needle or other delivery device into the subject at an appropriate location such as a vein, an artery, or the targeted tissue. For mice, the tail vein is commonly used. The user may secure the needle to the subject using, for example, medical tape, and the needle and needle tube may be primed to introduce blood into the needle and needle tube. A primed extension tube or primed diffusion chamber may be connected to the needle and needle tube to provide a wet-wet connection. The fluid may be delivered to the subject by activating the one or more driving devices 162 causing the plunger 155 to be advanced, thereby delivering the appropriate volume of fluid to the subject.

In some embodiments, another injection of the fluid may be delivered to the subject. In such embodiments, the procedure may continue by repeating the operations provided above. Notably, the initialization operations may be omitted during repeated delivery of fluid. In some embodiments, the fluid delivery system 100 may determine that the pressure and/or flow response in the targeted tissue should be adjusted and may adjust the pressure and rate of transmission accordingly. In the event that no further injections are necessary, the procedure may be terminated using a shutdown protocol, which may include flushing the system with medical fluid.

Figure 8:
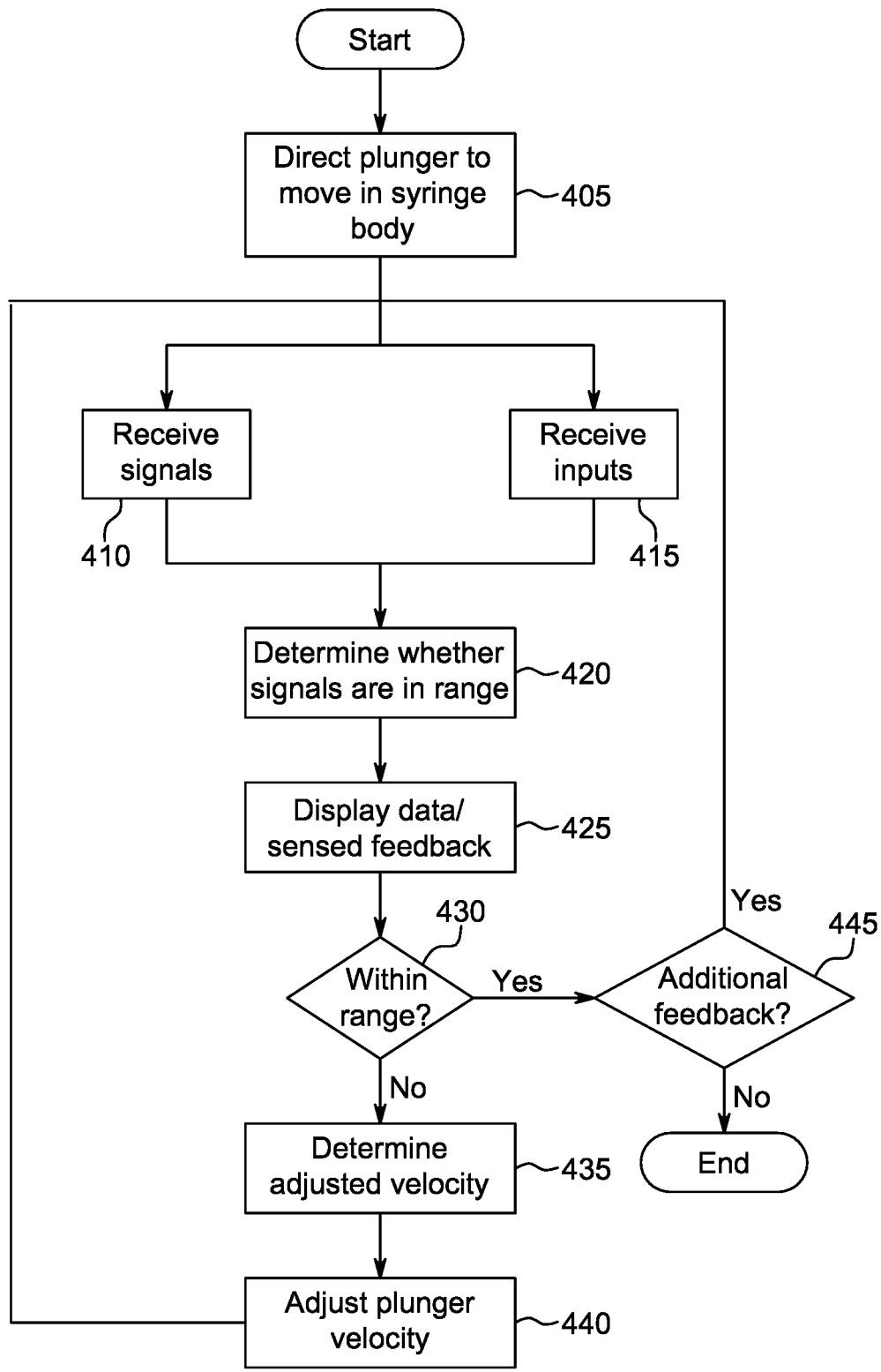
FIG. 8 depicts a flow diagram of a method of operating a fluid delivery system according to an embodiment

FIG. 8 depicts a flow diagram of a method of operating the fluid delivery system 100 (FIG. 1) according to an embodiment. In some embodiments, a processor may be connected to a non-transitory, processor-readable storage medium that contains one or more programming instructions that, when executed, cause the processor to complete the method described herein.

In various embodiments, the processor may direct 405 the plunger to move in the syringe body. In particular embodiments, the plunger may move in a distal direction to cause distribution of fluid to targeted tissue, as described in greater detail herein. The processor may direct the plunger to move at a particular velocity to ensure proper movement to the targeted tissue and/or a desired pressure is maintained in the fluid. As previously described herein, the plunger and the syringe body may be in the form of a pump, where the processor directs 405 the pump to distribute the fluid to the targeted tissue. In some embodiments, the processor may direct 405 the plunger by activating one or more driving devices that cause the actuation component to apply a force to the pump or plunger.

As the fluid is directed to the targeted tissue, the processor may receive 410 one or more signals from an intracorporeal sensing systems that has one or more sensor at or near the targeted tissue that correspond to one or more sensed feedback parameters sensed by the sensors of the intracorporeal sensing system. In some embodiments, the sensors may be located at or near the targeted tissue, and may be configured to sense the targeted tissue in real time. The processor may receive 410 the signals immediately prior to the sensing, as described herein. In addition to receiving 410 one or more signals, the processor may receive 415 one or more inputs. The inputs may be received from a user, program code, and/or the like, and may generally contain information regarding acceptable ranges for the sensed tissue, which is based upon the type of tissue being sensed and certain characteristics of the subject, as described herein.

The computing device may determine 420 whether the one or more sensed feedback parameters are within the acceptable ranges, and may optionally display 425 the sensed feedback and the acceptable range on a display. If the sensed feedback parameters are determined 430 to be within the acceptable range, the process may determine 445 whether any additional feedback is sensed by the sensors. If additional feedback is sensed, the processes may repeat. If no additional feedback is sensed, the processes may end.

If the computing device determines 430 that the feedback parameters are not within the acceptable range, it may determine 435 an adjusted velocity necessary to bring the feedback parameters within the acceptable range. The computing device may determine 435 the adjusted velocity via any number of inputs, via a preprogrammed algorithm, and/or the like, as previously described herein. The computing device may adjust 440 the plunger velocity by sending a signal to the plunger and/or the one or more driving devices to adjust the velocity accordingly. As the velocity is changed, the computing device may actively receive additional signals and the processes described herein may repeat until the feedback parameters are within the acceptable range. The processes described herein may be continuous and active, with the processor continuously receiving signals and adjusting velocity until the fluid delivery process is complete.

EXAMPLES

Example 1: Injector Control

The injector described in this Example is designed to allow more sophisticated and flexible types of control over injection procedures than is available with current injectors. As a result, the injector may aid in the discovery of new medical procedures and enable the consistent performance/delivery of an optimal procedure to each patient.

Injection control systems can be arrayed in a hierarchy from simplest to most complex. The following level designations are for reference only. Simplest is a gravity infusion with no control system, where the fluid is allowed to freely run into the patient. Second is a manual infusion, such as by using, for example, a handheld or hand-operated syringe. Some control is possible, but it is not consistent and cannot be long term. A next level is a fixed pressure with a restriction, such as, for example, a gravity-driven flow with a restriction. The fixed pressure with a restriction is often user-adjustable, and the flow rate is estimated by controlling a drop rate. Next is an electromechanical system, preferably with a computer-controlled user interface and operation. A simple stepper motor driven syringe pump is one example. There is no feedback loop, and there can be some safety checks. More sophisticated systems are able to deliver higher levels of control using feedback loops within the system to servo control the delivery to allow adjustment to external variations in aspects such as fluid path restrictions or back pressure build-up. Most current power injectors are capable of this type of operation.

Providing a measurement in the physiological system allows feedback to control a physiologically relevant parameter that can help ensure that delivery is sufficient for the desired goal but is not excessive so as to cause damage or other phenomena. Potential feedback parameters include, for example, pressure in the receiving vessel, pressure in tissue, temperature in a vessel, temperature in tissue, flow in a vessel, a property of an image such as density of a voxel, tissue stretch, tissue conductivity, tissue ultrasound properties, flow rate in the targeted tissue, a fluid cell count, a fluid particle count, the density of a measurable tracer, and the like. As is known in the medical arts, the property being measured by an imager depends upon the type of the imager, such as, for example, X-ray attenuation in CT imaging and proton density, T1, or T2 in MR imaging.

A second dimension or aspect to control is the one or more variables that are being controlled. Normal injections control flow rate until a total volume is delivered or a specified time period is met. A more sophisticated control also allows setting the acceleration or ramp by the user or the system (for example, to reduce catheter whip in angiography). If the injector can deliver multiple fluids in one injection, the composition or ratio is a variable that can be controlled to provide a better result for the patient. It is possible to control pressure as the primary parameter. An angioplasty balloon controller would have this function, where the fluid is delivered to inflate the balloon, but the amount or volume of fluid is not the primary parameter of importance. The parameters would be pressure and time, preferably with controlled ramp up and ramp down in pressure. The parameter being controlled or optimized can be received from a sensor or from an imager. In the current system, pressure feedback from the liver vein fits this category.

Controlling one parameter with a limit to or on a second parameter provides yet another level of control. Some current injectors control flow rate with a maximum pressure limit that can be set by the user. In an angioplasty, controlling pressure with a maximum volume to be delivered would result in an acceptable algorithm to resolve a leaking balloon issue. For example, in CT injections, delivering a flow rate of 10 ml/second with a pressure limit of 100 psi means that the fluid delivery system will deliver the fluid at 10 ml/second independent of the pressure needed, until it requires 100 psi or more. Then the fluid delivery system either limits the pressure at 100 psi and delivers less flow until the full volume selected is delivered, or may optionally halt the delivery because the pressure limit has been reached. The controller of this system provides further capability around limiting behavior in that the user may select more than one parameter to be used as a limit, such as, for example, programming an injection to achieve a certain intravascular pressure for a certain duration can have limits to both flow rate and volume delivered in that phase or overall. Another example is delivering a flow rate for a total volume with a limit on pressure in the vessel, pressure in the system or syringe, and time/duration. Limits, at the discretion of the user, are applied to each phase of the injection or procedure or to cumulative parameters such as time or volume for multiple phases. The control system of an embodiment provides a number of options to the user in regards to the actions that are taken when a limit is reached. As mentioned above, the simplest is to halt the injection when the a limit is reached. A second is to only alert the user that a limit has been reached and not change behavior in any way, unless a capability of the system has been reached. A third is to hold the limit parameters at their limits and reduce or extend other parameters to allow the procedure to continue to completion or until another limit is reached, with or without alerting the user real time. A fourth option is to alert the user and require some action within a certain timeframe, such as, for example, stopping unless the user presses a continue button. The type of interaction may depend upon the type of user control. The real time information or feedback to the operator includes alerting the user when limits are being approached so that limiting behavior is averted.

The next level of control allows different parameters to be controlled during different phases or times during the injection or procedure with other parameters being in the limit role. When flow rate or pressure is the controlled parameter that the system seeks to maintain within the operator defined range, one or more controlled parameters in each phase are used. The system used one or more action parameters to adjust and keep the controlled parameters within the range. For example, the pump would increase flow rate if the intravascular pressure is lower than the target range. Increased flow rate is achieved by increasing the motor current and/or the voltage to the pump, which are commonly parameters not visible to the user. Thus, flow rate, motor voltage, and motor current are action parameters. Furthermore, one or more duration parameters are used to determine the duration or completion of the phase or injection. In addition, one or more limiting parameters are set to help assure safe or proper operation of the system. There are also one or more monitor or measured parameters which the system assesses or measures and reports to the user, use in the control algorithm or process (for example, to anticipate conditions) or use in some other way. The user may not be aware of the system's action or measured parameters. Thus, with the injector described herein, a volume of gene therapy fluid (the duration parameter) is first delivered at a low or moderate flow rate (the controlled parameter) with a relatively low in-vein pressure limit (a limiting parameter) to ensure that the liver vessels are filled with the gene therapy fluid and not blood or contrast, and optionally with a set syringe pressure limit (a second limiting parameter) to ensure safe operation. The second phase of the procedure ramps up the flow rate quickly (the controlled parameter) to build up pressure in the vein (a duration parameter) and drive the fluid into the tissue with a venous pressure limit (a limiting parameter) to prevent damage. The transition to the third phase occurs when a certain venous pressure is achieved (duration parameter for the second phase). The venous pressure (controlled parameter) is held for a time (duration parameter) to maintain the "stretch" and enable the fluid to diffuse into the extravascular space, with a flow rate limit (limit parameter) in case there is too much leakage, and optionally with a flow rate limit (limit parameter) as well. The final phase is a venous pressure ramp (controlled parameter) down over a time (duration parameter) to consistently and controllably return the system to normal pressure. In this situation, the ability to select and vary the parameter that is being controlled, the duration parameter(s), and the parameter(s) that are serving as the limit(s) improves the ability to optimize and customize the injection. The transition between the second and third phase was based on achieving a pressure, and not a total volume delivered, time, or a flow rate achieved. This is another example of mixed controls, where the end of one phase and the beginning of another is determined by the value of an alternate control parameter.

Figure 9:
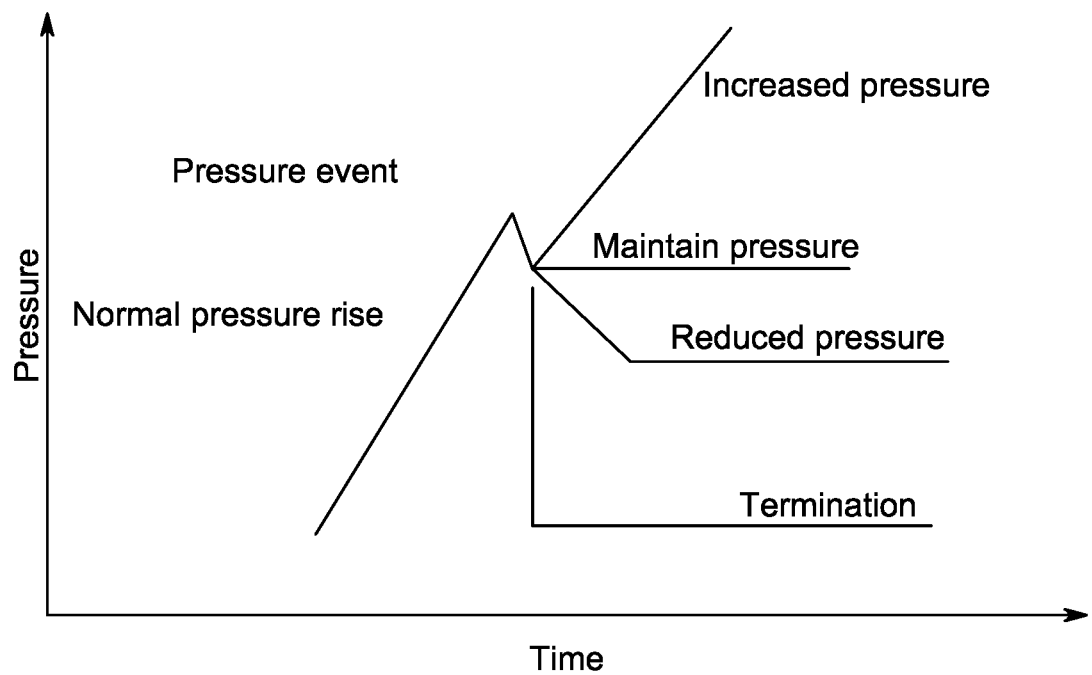
FIG. 9 depicts a schematic diagram of a method for detection of a drug extravasation according to an embodiment.

To achieve the next level of adjustment or control algorithm sophistication, duration parameters or limit parameters that are dependent upon or recognize the patient's physiological condition or response to the procedure are employed. FIG. 9 discloses such a situation. In the second phase described above where the flow rate and pressure in the vein rapidly increases, a sudden drop in pressure may result where the liver "cracks" or the gateway to an alternative fluid path opens, such as to the arterial flow. In this case, the system can automatically enter a next phase that maintains that pressure for a fixed time. Alternatively, in that next phase, the pressure could be slowly decreased or increased, as shown in FIG. 9. The particular action to be performed will be a function of the specific physiology and procedure for which the system is being used.

Example 2: Liver Phantom Test Injection Using a Dog Liver Pressure Profile

A Medrad Mark V ProVis® Injection System (Bayer HealthCare, Indianola Pa.) was used to inject fluid into a liver phantom model. The liver phantom model was constructed to mimic a typical dog liver under various biological conditions. The device, constructed as a controlled and programmable pressurized chamber is used to simulate the pressure and flow characteristics of the targeted organ or region of interest. An injection protocol is programmed into the injection system, then the fluid media is injected into the phantom. As the programmed injection is delivered to the phantom, the results are captured by the installed phantom sensors, such as, but not limited to, pressure sensors, fluid flow sensors, and temperature sensors. The data is then saved in memory and charted for the user to read, evaluate and manipulate. The user can then use the recorded results to modify or improve the programmed injection as necessary or desirable.

Pressure of the fluid in the phantom model was introduced using a Mentor™ Pressure Simulator (Merit Medical, South Jordan Utah), and the pressure of the phantom model was sensed using a PCU-2000 Pressure Control Unit (Millar Instruments Inc., Houston Tex.). Fluid was injected into the phantom liver at a rate of 0-40 ml/second for 6 seconds to deliver 120 ml of fluid, and then was injected at a rate of 40 ml/second for 2 second to deliver 80 ml of fluid through an 8 French catheter. A similar process was carried out in a live animal model. A standard image-guided insertion procedure employed in the clinic was used for placing a balloon catheter into the right lateral hepatic vein or renal vein to target the liver or kidney, respectively. The total injection volume was 800 ml delivered in 20 seconds (40 ml/s) for the liver, and 55 ml in 11.7 seconds (4.7 ml/s) for the kidney.

Figure 10A:
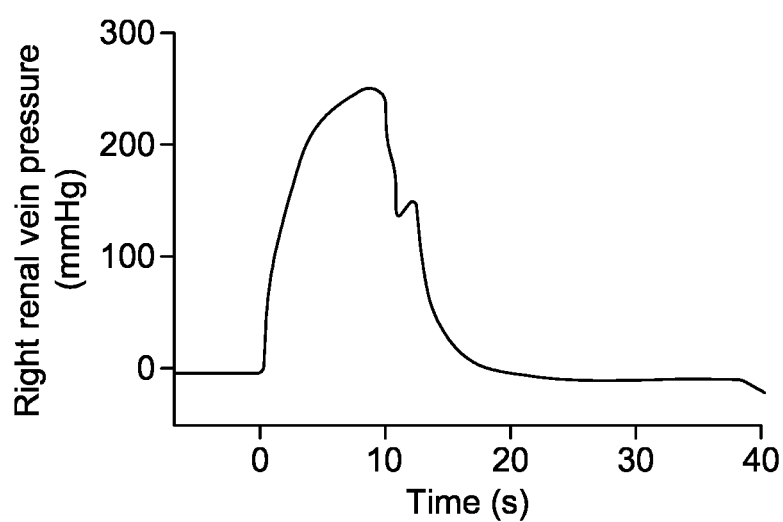
FIG. 10A depicts a graphical illustration of a change in pressure in liver tissue of a dog over a period of time according to an embodiment.
Figure 10B:
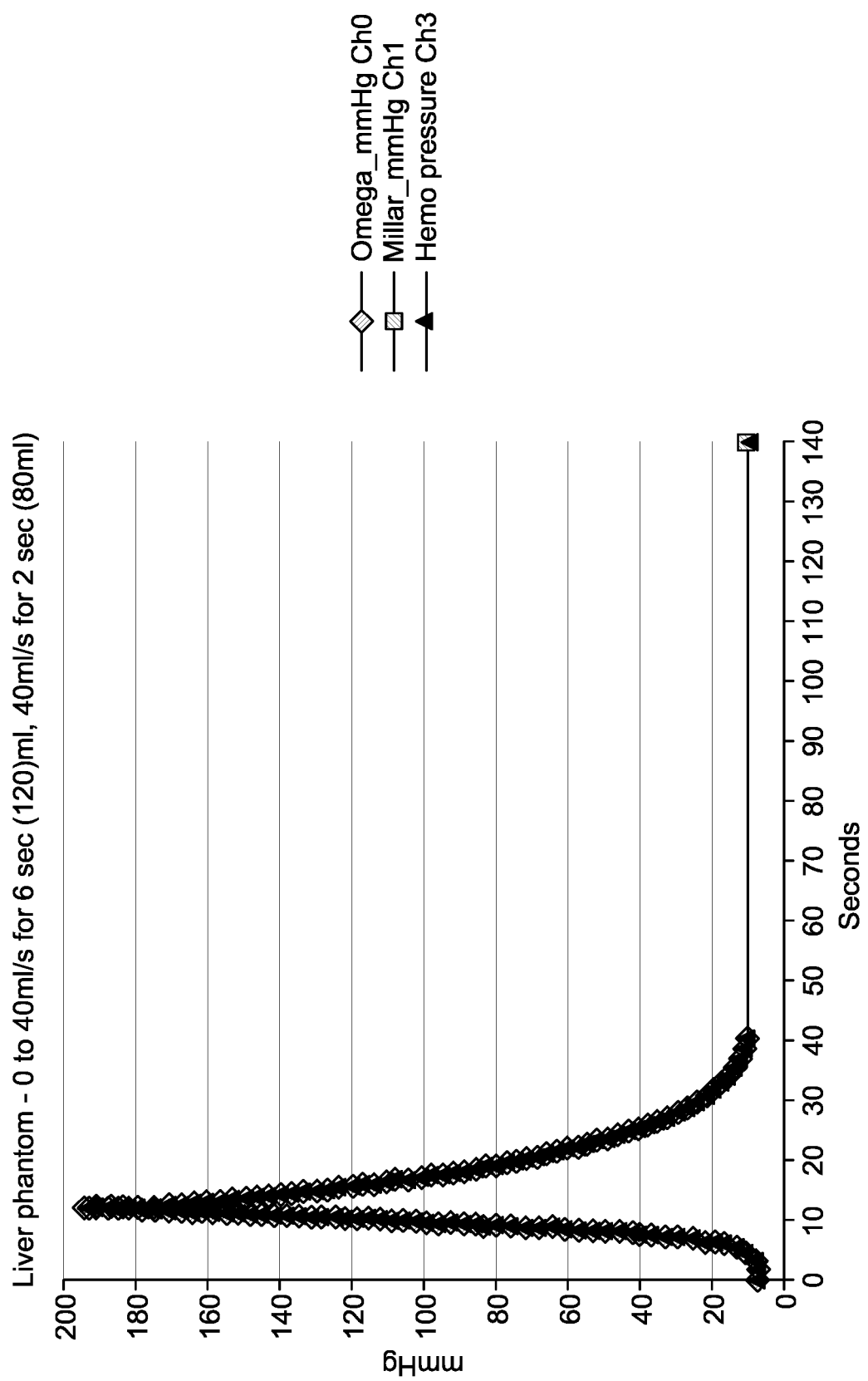
FIG. 10B depicts a graphical illustration of a change in pressure in a phantom liver over a period of time according to an embodiment.

Results of the test are displayed in FIGS. 10A and 10B. The results show that the waveforms are generally the same and can be tuned to be identical by changing parameters of the liver phantom.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

The invention claimed is:

1. A system for delivering a fluid to a targeted tissue in accordance with an injection protocol having at least two phases, the system comprising:
   a pump configured to contain a volume of the fluid;
   a sensing system;
   a processor in operable communication with the pump and the sensing system, wherein the processor is configured to:
      control the pump to deliver the fluid to the targeted tissue based on a first predetermined value of a first controlled parameter in accordance with each of a first phase and a second phase of the injection protocol;
      during each of the first phase and the second phase, receive one or more signals from the sensing system corresponding to a first limiting parameter, wherein the first limiting parameter comprises at least one of: a pressure at the pump, a flow rate at the pump, a pressure in a receiving vessel, a pressure in the targeted tissue, an image property, a tissue stretch property, a tissue conductivity, a tissue ultrasound property, a flow rate in the targeted tissue, a fluid cell count, a fluid particle count, and a density of a measurable tracer;
      during each of the first phase and the second phase, determine whether the first limiting parameter is outside an acceptable range of the first limiting parameter;
      during each of the first phase and the second phase, determine an adjusted value of the first controlled parameter in response to determining that the first limiting parameter is outside the acceptable range of the first limiting parameter; and during each of the first phase and the second phase, control the pump to deliver the fluid to the targeted tissue based on the adjusted value of the first controlled parameter,
   wherein the acceptable range of the first limiting parameter is different during the first phase than during the second phase.

2. The system of claim 1, wherein the first controlled parameter comprises at least one of an injection pressure, an injection flow rate, an injection volume, the pressure in the targeted tissue, and the flow rate in the targeted tissue.

3. The system of claim 1, wherein the acceptable range of the first limiting parameter is based on at least one of a threshold at which the targeted tissue will be damaged and a mechanical capacity of the pump.

4. The system of claim 1, wherein the processor is further configured to:
   control the pump to deliver the fluid to the targeted tissue based on a second predetermined value of a second controlled parameter, and
   wherein the second controlled parameter is equal to or different than the first controlled parameter.

5. The system of claim 1, wherein the one or more signals further correspond to a duration parameter, wherein the duration parameter comprises at least one of: an injection time, the pressure at the pump, the flow rate at the pump, the pressure in the receiving vessel, the pressure in the targeted tissue, the image property, the tissue stretch property, the tissue conductivity, the tissue ultrasound property, the flow rate in the targeted tissue, the fluid cell count, the fluid particle count, and the density of the measurable tracer, and
   wherein the processor is further configured to:
   determine that a target value of the duration parameter has been met; and
   control the pump to distribute the fluid to the targeted tissue based on a second predetermined value of a second controlled parameter in accordance with the second phase of the injection protocol.

6. The system of claim 5, wherein the second controlled parameter is equal to or different than the first controlled parameter.

7. The system of claim 1, wherein controlling the pump to distribute the fluid to the targeted tissue comprises controlling the pump to distribute the fluid to the targeted tissue at a pressure of about 10 psi to about 2000 psi.

8. The system of claim 1, wherein the processor is further configured to:
   generate an alert to a user in response to determining that the first limiting parameter is outside the acceptable range; and
   control the pump to halt the injection protocol in response to not receiving from the user a response to the alert.

9. A computer-implemented method for automatically delivering a fluid to a targeted tissue in accordance with an injection protocol having at least two phases, the method comprising:
   controlling, by a processor, a pump to distribute the fluid to the targeted tissue based on a first predetermined value of a first controlled parameter in accordance with each of a first phase and a second phase of the injection protocol;
   receiving, by the processor during each of the first phase and the second phase, one or more signals from a sensing system corresponding to a first limiting parameter, wherein the first limiting parameter comprises at least one of: a pressure at the pump, a flow rate at the pump, a pressure in a receiving vessel, a pressure in the targeted tissue, an image property, a tissue stretch property, a tissue conductivity, a tissue ultrasound property, a flow rate in the targeted tissue, a fluid cell count, a fluid particle count, and a density of a measurable tracer;
   determining, by the processor during each of the first phase and the second phase, that the first limiting parameter is outside an acceptable range of the first limiting parameter;
   determining, by the processor during each of the first phase and the second phase, an adjusted value of the first controlled parameter in response to determining that the first limiting parameter is outside the acceptable range of the first limiting parameter; and
   controlling, by the processor during each of the first phase and the second phase, the pump to distribute the fluid to the targeted tissue based on the adjusted value of the first controlled parameter,
   wherein the acceptable range of the first limiting parameter is different during the first phase than during the second phase.

10. The computer-implemented method of claim 9, wherein the first controlled parameter comprises at least one of an injection pressure, an injection flow rate, an injection volume, the pressure in the targeted tissue, and the flow rate in the targeted tissue.

11. The computer-implemented method of claim 9, wherein the acceptable range of the first limiting parameter is based on at least one of a threshold at which the targeted tissue will be damaged and a mechanical capacity of the pump.

12. The computer-implemented method of claim 9, further comprising controlling, by the processor, the pump to deliver the fluid to the targeted tissue based on a second predetermined value of a second controlled parameter,
   wherein the second controlled parameter is equal to or different than the first controlled parameter.

13. The computer-implemented method of claim 9, wherein the one or more signals further correspond to a duration parameter, wherein the duration parameter comprises at least one of: an injection time, the pressure at the pump, the flow rate at the pump, the pressure in the receiving vessel, the pressure in the targeted tissue, the image property, the tissue stretch property, the tissue conductivity, the tissue ultrasound property, the flow rate in the targeted tissue, the fluid cell count, the fluid particle count, and the density of the measurable tracer, and
   wherein the method further comprises:
   determining, by the processor, that a target value of the duration parameter has been met; and
   controlling, by the processor, the pump to distribute the fluid to the targeted tissue based on a second predetermined value of a second controlled parameter in accordance with the second phase of the injection protocol.

14. The computer-implemented method of claim 13, wherein the second controlled parameter is equal to or different than the first controlled parameter.

15. The computer-implemented method of claim 9, wherein controlling the pump to distribute the fluid to the targeted tissue comprises controlling the pump to distribute the fluid to the targeted tissue at a pressure of about 10 psi to about 2000 psi.

16. The computer-implemented method of claim 9, further comprising:
   generating, by the processor, an alert to a user in response to determining that the first limiting parameter is outside the acceptable range; and controlling, by the processor, the pump to halt the injection protocol in response to not receiving from the user a response to the alert.

\* \* \* \* \*

UNITED STATES PATENT AND TRADEMARK OFFICE
CERTIFICATE OF CORRECTION

PATENT NO. : 11,648,346 B2
APPLICATION NO. : 16/687034
DATED : May 16, 2023
INVENTOR(S) : Uber, III et al.

It is certified that error appears in the above-identified patent and that said Letters Patent is hereby corrected as shown below:

In the Specification

In Column 1, Line 7, delete "filed Mar. 15, 2013," and insert -- filed Dec. 12, 2016, now U.S. Pat. No. 10,478,558, issued Nov. 19, 2019, --, therefor.
In Column 2, Line 45, delete "may" and insert -- may be --, therefor.
In Column 5, Line 11, delete "closes" and insert -- closest --, therefor.
In Column 5, Line 50, delete "(ATL)" and insert -- (ALT) --, therefor.
In Column 5, Line 52, delete "ATL" and insert -- ALT --, therefor.
In Column 7, Line 60, delete "injected" and insert -- injection --, therefor.
In Column 7, Line 60, delete "vary" and insert -- very --, therefor.
In Column 8, Line 35, delete "napthalate" and insert -- naphthalate --, therefor.
In Column 9, Line 20, delete "0-rings" and insert -- O-rings --, therefor.
In Column 9, Line 60, delete "securably" and insert -- securely --, therefor.
In Column 11, Line 15, delete "mechanism 173" and insert -- mechanism 172 --, therefor.
In Column 13, Line 3, delete "capability" and insert -- capability. --, therefor.
In Column 14, Line 29, delete "1) For" and insert -- 1). For --, therefor.
In Column 17, Line 24, delete "device 100" and insert -- device 120 --, therefor.
In Column 18, Line 53, delete "and or" and insert -- and/or --, therefor.
In Column 22, Line 35, delete "the a" and insert -- the --, therefor.

Signed and Sealed this
Twenty-fifth Day of July, 2023

Katherine Kelly Vidal
*Director of the United States Patent and Trademark Office*